United States Patent [19]

Hamanaka

[11] 3,933,797
[45] Jan. 20, 1976

[54] 6-[α-(ω-QUANIDINOALKANOYLAMIDO)ACYLAMIDO]PENICILLANIC ACIDS

[75] Inventor: Ernest S. Hamanaka, Groton, Conn.

[73] Assignee: Pfizer Inc., New York, N.Y.

[22] Filed: Sept. 23, 1974

[21] Appl. No.: 508,070

Related U.S. Application Data

[62] Division of Ser. No. 228,344, Feb. 22, 1972, Pat. No. 3,870,709.

[52] U.S. Cl. .......................................... 260/239.1
[51] Int. Cl.$^2$ ................................... C07D 499/44
[58] Field of Search ............................. 260/239.1

[56] References Cited
UNITED STATES PATENTS

| | | | |
|---|---|---|---|
| 3,433,784 | 3/1969 | Long et al. | 260/239.1 |
| 3,634,405 | 1/1972 | Holdrege | 260/239.1 |
| 3,711,471 | 1/1973 | Kaplan | 260/239.1 |

*Primary Examiner*—Gerald A. Schwartz
*Attorney, Agent, or Firm*—Connolly and Hutz

[57] ABSTRACT

6-[α-(ω-guanidinoalkanoylamido)acylamido]penicillanic acids, the non-toxic salts and esters thereof are useful as antibacterial agents, therapeutic agents in animals, including man, of particular value against gram-negative bacteria, and as animal feed nutritional supplements.

7 Claims, No Drawings

6-[α-(ω-QUANIDINOALK-ANOYLAMIDO)ACYLAMIDO]PENICILLANIC ACIDS

CROSS REFERENCE TO RELATED APPLICATION

This application is a division of application Ser. No. 228,344 filed Feb. 22, 1972 and now U.S. Pat. No. 3,870,709.

BACKGROUND OF THE INVENTION

1. Field of the Invention

This invention relates to novel antibacterial agents; namely, (substituted acyl)derivatives of α-aminoacyl penicillins. More particularly, it is directed to 6[α-(ω-guanidinoalkanoylamido)acylamido]penicillanic acids, the non-toxic salts and esters thereof, which are especially useful in the treatment of gram-negative infections and, particularly, Pseudomonas infections.

2. Description of the Prior Art

A large number of 6-[(α-aminoacylamido)penicillanic acids wherein the acyl moiety is alkanoyl or substituted alkanoyl wherein the substituent is an aryl, cycloalkyl or heterocyclic group are disclosed in U.S. Pats. 2,985,648; 3,007,920; 3,192,198; 3,485,819; 3,342,677; 3,538,083; 3,553,201; British Patents 873,049; 903,785; 991,586; 1,033,257 and 1,189,990. Further, 6-[α-substituted amino)acylamido]penicillanic acids are described in U.S. Patents 3,198,788; 3,248,387; 3,308,023; 3,320,240; 3,325,477; 3,340,252; 3,381,001; 3,433,784; 3,518,253; British patents 891,977; 894,457; 985,688; 1,048,907; 1,051,675; 1,057,697; 1,064,893; 1,066,107; 1,125,339; 1,180,745; 1,210,472; Belgian Patent 593,295 and Japanese Patent 7,116,994. Additionally, 6-(α-ureido acylamido)penicillanic acids are disclosed in U.S. Pat. 3,352,851 and German Patent 2,054,772; 6-(α-guanidinoacylamido)penicillanic acids in U.S. Pats. 3,454,557 and 3,406,185; and a variety of p-quanidinoaroyl-,p-quanidinomethylaroyl-and p-guanidinoarylalkanoylamidopenicillanic acids are disclosed in U.S. Pat. 3,453,265. British Patent 1,061,335 discloses 6-(D-α-hydrazinocarbonylamino-α-phenylacetamido)penicillanic acid, and British Patent 1,053,818 describes esters of 6-(α-oxalamidoacylamido)penicillanic acids.

A wide variety of 6-[α-(3-substituted ureido)acylamido]penicillanic acids and 6-[α-(3-substituted thioureido) acylando-]penicillanic acids are reported in the recent literature. U.S. Patents 3,479,339; 3,481,922; Netherlands Patents 69,01646; 69,08909; and Japanese Patent 7,112,732 describe such compounds wherein the 3-substituent is a carbamoyl group; the compounds being referred to as 6-[α-(3-allophanamido)acylamido]penicillanic acids. U.S. Pat. 3,579,501 discloses 6-[α-(3-guanylureido)acylamido]-penicillanic acids; that is, such compounds wherein the 3-substituent is a guanyl moiety.

The above described products are active as antibacterial agents against a variety of gram-positive and gram-negative bacteria. However, while they are active in vitro and in vivo via the intraperitoneal route of administration, they are inactive or, at best, poorly active in vivo via the oral route of administration. Additionally, their pharmaco-kinetics, as evidenced by levels of the compound in the blood, are poor.

SUMMARY OF THE INVENTION

There has now been found a novel series of antibacterial agents; namely, 6-[α-(ω-guanidinoalkanoylamido)acylamido]penicillanic acids of the formula

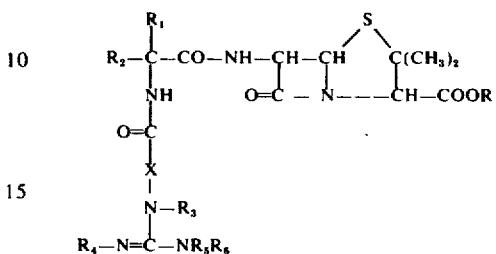

and the pharmaceutically acceptable acid addition salts thereof wherein R is selected from the group consisting of hydrogen and acyloxy lower alkyl wherein acyloxy is selected from the group consisting of lower alkanoyloxy, benzoyloxy and substituted benzoyloxy wherein the substitutent is selected from the group consisting of chloro, bromo, fluoro, lower alkyl, lower alkoxy and trifluoromethyl;

$R_1$ is selected from the group consisting of hydrogen, alkyl of 1 to 14 carbon atoms, cycloalkyl of 3 to 6 carbon atoms, 1,4-cyclohexadienyl, naphthyl, benzyl phenethyl, indolylmethyl, furyl, thienyl, ω-ethylthio(-lower alkyl and

wherein Y is selected from the group consisting of hydrogen, nitro, di(lower alkyl)amino, lower alkanoylamino, lower alkyl, lower alkoxy, hydroxy, sulfamyl, chloro, bromo, fluoro, iodo and trifluoromethyl;

$R_2$ is selected from the group consisting of hydrogen and lower alkyl;

$R_1$ and $R_2$ when taken together with the carbon atom to which they are attached are cycloalkylidene of 3 to 10 carbon atoms;

each of $R_3$, $R_4$, $R_5$ and $R_6$ is selected from the group consisting of hydrogen, lower alkyl, benzyl and phenyl;

$R_4$ and $R_5$ when taken together with the guanyl moiety to which they are attached form a 5- or 6-membered heterocyclic ring selected from the group consisting of 2-imidazolyl, 2-(2-imidazolinyl), 2-(1,4,5,6-tetrahydropyrimidinyl) and 2-pyrimidinyl;

X is selected from the group consisting of alkylene having from 1 to 7 carbon atoms, phenylene cycloalkylene having from 3 to 9 carbon atoms, propenylene whose —CH₂ group is bound to the adjacent nitrogen vinylenephenylene, methylene oxyphenylene and phenylenemethylene, each of whose phenylene group is bound to the adjacent nitrogen;

X and N—$R_3$ when taken together form a 5- or 6-membered heterocyclic ring selected from the group consisting of pyrrolidyl and piperidyl;

X and $R_5$ when taken together with the guanidino moiety to which they are attached form a 5- or 6-membered heterocyclic ring selected from the group consisting of 2-amino-2-imidazolinyl and 2-amino-2-(1,4,5,6-tetrahydropyrimidinyl);

$R_3$ and $R_4$ when taken together with the guanidino moiety to which they are attached form a 5- or 6-membered heterocyclic ring selected from the group consisting of 2-imidazolino and 2-(1,4,5,6-tetrahydropyrimidino); and $R_3$ and $R_5$ when taken together with the guanidino moiety to which they are attached form a 5- or 6-membered heterocyclic ring selected from the group consisting of imidazolidino and hexahydropyrimidino.

Included among the pharmaceutically acceptable acid addition salts of this invention are inorganic and organic acid addition salts. Typical salts include hydrochloride, hydrobromide, hydroiodide, sulfate, phosphate, acetate, citrate, benzoate, maleate, succinate, malate, fumarate, ascorbate, glycolate, tartrate, oxalate and mandelate.

Also included within the scope of this invention are the optically active isomeric forms and mixtures thereof which arise by virtue of the asymmetric α-carbon atom of the acyl side chain. These are the D- and the L-diastereoiosmers and the DL-form which is a mixture of the two optically active isomers. The D-form of these compounds is the preferred form because of its greater activity relative to that of the L- or the DL-forms.

Other isomers of the herein described compounds in addition to those arising from the asymmetric α-carbon of the acyl side chain are, of course, possible because of the presence of asymmetric carbon atoms in the 6-aminopenicillanic acid nucleus.

The novel antibacterial products of this invention are of value as additives to materials such as fuels and cutting oils which are subject to bacterial deterioration and are useful in soaps and shampoos and in topical compositions for treatment of wounds. They are also remarkably effective in treating a number of infections caused by susceptible gram-negative and gram-positive bacteria in poultry and animals, including man.

DETAILED DESCRIPTION OF THE INVENTION

The novel and valuable compounds of this invention are prepared by reacting an appropriate 6-[(α-amino-substituted)acylamido]penicillanic acid, or a suitable ester thereof, of the formula

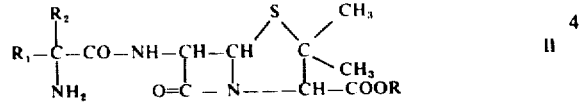

with a reactive functional derivative of the carboxy group of an appropriate guanidino substituted acid of the formula

wherein the variables X, R and $R_1$ - $R_6$ are as defined above, and Z is hydroxy or a halo group.

Alternatively, compounds of formula I, especially those wherein X is alkylene, can be prepared by reacting a compound of formula III-A

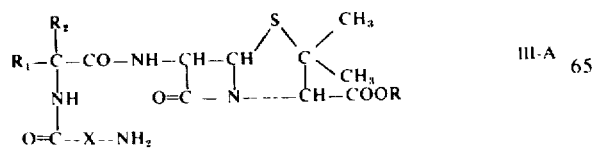

with an appropriate S-alkylisothiourea of formula III-B

according to standard procedures.

The terms "lower alkyl, lower alkoxy and lower alkanoyloxy" as used herein are intended to include those alkyl, alkoxy and alkanoyloxy groups having from one to four carbon atoms.

Suitable esters of the formula II reactants are those wherein R is acyloxy lower alkyl as defined above and those wherein R is a group which can readily be removed as, for example, by catalytic hydrogenation (benzyl, cyanomethyl, phenacyl, allyl and diphenylmethyl).

Suitable reactive functional derivatives of acids of formula III are the acid chlorides or bromides (Z = Cl, Br). The acid reactant can be reacted with a "condensing" agent such as a carbodiimide, an alkoxyacetylene, N,N'-carbonyldiimidazole, N,N'-carbonylditriazole and hexahalocyclotriphosphatriazines to give a reactive intermediate which is coupled to the 6-[(α-amino substituted)acylamido]penicillanic acid. Additionally, the appropriate acid azide or an active ester or thio ester of the formula III reactant with, for example, N-hydroxyphthalimide, N-hydroxysuccinimide, a phenol or thiophenol can be used as acylating agent.

The preferred acylation processes of this invention comprise the reaction of the appropriate 6-[(α-amino substituted)acylamido]penicillanic acid compound (formula II) with the acid chloride of an acid of formula III, or with the acid form of a formula III reactant in the presence of a carbodiimide for reasons of convenience, availability of reactants and overall yield of product.

The 6-[(α-amino substituted)acylamido]penicillanic acid reactant can be used in a variety of forms. It can, for example, be used as the free acid or as an alkali metal or amine salt thereof. The use of a salt form of the penicillanic acid reactant is frequently of advantage since the solubility can be manipulated by judicious choice of the salt to permit the use of aqueous or non-aqueous systems. Alkali metal salts are valuable for use in aqueous systems. In non-aqueous systems, an amine salt such as a tertiary lower alkylamine salt, e.g., triethylamine, or an N-alkyl piperidine salt is generally used. Alternatively, an ester of the 6-[(α-amino substituted-)acylamido]penicillanic acid is used, especially in non-aqueous systems. In those instances wherein the final product (formula I) is desired in the form of an ester (R is other than hydrogen), it is obvious and practical to use that ester form of the penicillanic acid reactant.

The acylation process is conducted in a reaction-inert solvent system which can be aqueous or non-aqueous. Aqueous or non-aqueous solvent systems can be used when a carbodiimide is the condensing agent. When using a carbodiimide in an aqueous system, the pH is desirably adjusted to the range of about 5 to about 8, and preferably to about 6 to 7. In a typical procedure, the formula III reactant and carbodiimide are mixed in equimolar proportions in a suitable solvent (tetrahydrofuran, dioxan) and a water-water-miscible organic solvent solution (water plus dioxan or tetrahydrofuran) containing the 6-[α-amino substituted)acylamido]penicillanic acid is added at room temperature and the mixture stirred for several hours until reaction is complete. Temperatures of from about −5° to 30° C. are generally used. In most instances, an excess up to about 10% of the condensing agent is used. The penicillin product is recovered by methods known to the art.

Acylation with an acid halide (formula III) can also be conducted in aqueous or non-aqueous solvent systems. In aqueous systems, the reaction is generally carried out at a pH of from about 6 to about 9 and a temperature of from about 0° C. to about 50° C. It can also be preformed in unstable emulsions of water and a water-immiscible organic solvent such as methyl isobutyl ketone and lower alkyl acetates over the pH range of from about 2 to about 4.

In addition to the above purely chemical technique of acylation, a sonochemical technique; that is, the application of vibrations of ultrasonic frequency (35,000 to 90,000 cycles per second), as described in U.S. Pat. 3,079,314, issued Feb. 26, 1963, can also be used to achieve acylation of the 6-[(α-amino substituted-)acylamido]penicillanic acid, especially acylation with an acid halide. Acylation under such conditions is rapid and permissive of a wide range of reaction media, aqueous and nonaqueous alike, homogeneous and non-homogeneous, including emulsified systems.

The esters of this invention, compounds of formula I wherein R is acyloxy(lower alkyl), can be prepared by reacting an alkali metal salt (sodium, potassium, lithium) of a compound of formula I wherein R is hydrogen and $NR_5R_6$ is $NHNO_2$ with the appropriate acyloxy(lower alkyl) halide (chloride or bromide). The reaction is normally conducted in a reaction-inert solvent such as tetrahydrofuran, dimethylformamide, dimethylsulfoxide or hexamethylphosphoramide. In practice, the halide is added, usually dropwise, to a solution or suspension of an alkali metal salt of the nitroguanidino compound. At least one equivalent of the halide reactant is added but, in certain cases, it may be advantageous to employ as much as a 50 percent excess. The reaction is carried out at temperatures of from 0° to 50°C. and preferably from 20° to 30° C. Reaction time will vary according to the temperature employed and the reactivity of the appropriate starting materials. Normally, the reaction period will range from one to twenty hours. The nitroguanidino ester derivative thus produced is then catalytically hydrogenated to the corresponding guanidino ester of formula I. The nitroguanidino derivative of I (R=H, $NR_5R_6$=$NHNO_2$) is prepared by acylating the appropriate α-aminoacyl-penicillin with the appropriate nitroguanidino carboxylic acid by method described herein.

Alternatively, and preferably, the acyloxy(lower alkyl) esters of formula I compounds are prepared by the above described acylation procedures but using the appropriate acyloxy(lower alkyl) ester of the appropriate 6-[(α-amino substituted)acylamido]penicillanic acid in place of the non-esterified 6-[(α-amino substituted)acylamido]penicillanic acid. The acyloxy(lower alkyl) esters of the 6-[(α-amino substituted-)acylamido]penicillanic acids are prepared according to methods described in Belgian 721,515 and by Daehne et al., J. Med. Chem. 13, 607-612 (1970).

The acyloxy(lower alkyl) halides are synthesized from the corresponding acid chlorides and aldehydes or ketones in accordance with the general procedures of Ulich et al., J. Am. Chem. Soc. 43, 660 (1921) and Euranto et al., Acta. Chem. Scand. 20, 1273 (1966). The formation of esters from acid salts and alkyl halides is well documented in the chemical literature (Zook and Wagner, "Synthetic Organic Chemistry," John Wiley and Sons, Inc., New York, 1956, p. 484).

The 6-[(α-amino substituted)acylamido]penicillanic acid reactants are described in the art cited above.

Many of the guanidino substituted carboxylic acid reactants of the formula $HOOC-X-NR_3-C(=NR_4)-NR_5R_6$ are described in the literature. Particular reference is made to U.S. Pats. 3,257,411; 3,406,185 and 3,479,401 which describe such acids wherein X is phenylene, methylenephenylene, alkylene and cyclohexylene (see formula II). Those guanidino substituted acid reactants which are not known in the art are prepared from the corresponding amino substituted carboxylic acids by reacting the amino acid with S-methylisothionitrourea. The intermediate nitroguanidinocarboxylic acid is then catalytically hydrogenated to the desired guanidino substituted carboxylic acid.

An alternative and favored method for preparing guanidino-substituted carboxylic acid comprises reaction of the appropriate amino substituted carboxylic acid with benzoylcyanamid followed by hydrolysis of the benzoyl guanidino substituted reaction product.

A further method for preparing the guanidino-substituted carboxylic acids involves reaction of the appropriate amino substituted carboxylic acid with O-methylisourea, S-methylisothiourea or appropriate substituted isothiourea in alkaline solution.

Still another method for preparing compounds of formula I comprises acylating 6-aminopenicillanic acid or an appropriate ester thereof with a reactive functional derivative of an acid of formula IV according to the above described procedures

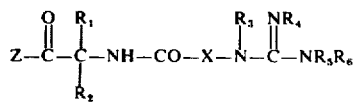

wherein X, $R_1-R_6$ and Z are as defined above. This method is not generally favored because the reactants are less readily available than are those of formula III. They can, of course, be prepared by methods known to those skilled in the art.

Examples illustrating the preparation of compounds within the scope of this invention are given below. In the formulae accompanying the examples, "-APA-" represents the moiety

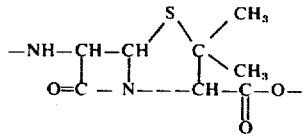

The guanidino moiety of the acyl side chain, for convenience, employs the following numbering system

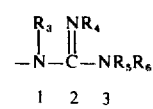

Tautomeric forms of the guanidino moiety wherein at least one of $R_3$, $R_4$, $R_5$ and $R_6$ is other than hydrogen are also embraced within this invention.

The novel penicillins described herein exhibit in vitro activity against a wide variety of both gram-positive and gram-negative bacteria, including indole-positive Proteus. Their useful activity can readily be demonstrated by in vitro tests against various organisms in a brain-heart infusion medium by the usual two-fold serial dilution technique. The in vitro activity of the herein-described compounds renders them useful for topical application in the form of ointments, creams and the like, or for sterilization purposes, e.g., sick room utensils.

The in vitro spectra of a number of 6-[α-(ω-guanidinoalkanoylamido)acylamido]penicillanic acids of this invention against certain gram-negative bacteria are presented in Table I below. D-α-aminobenzylpenicillin and 6-[D-2-phenyl-2-(3-guanylureido)acetamido]penicillanic acid are included for the purpose of comparison. The compounds of Table I have the formula ertheless, oral in vivo activity against *Escherichia coli.* and *Staphylococcus aureus* is a common property of many compounds of this invention. Table II below presents the comparative in vivo spectra of several compounds within the scope of this invention against D-α-aminobenzylpenicillin (Ampicillin). Table III presents comparative $PD_{50}$ values of 6-]D-2-phenyl-2-(guanidinoacetamido)acetamido]penicillanic acid [A], 6-[D-2-phenyl-2-(3-guanylureido)acetamido]-penicillanic acid [B] and D-α-aminobenzylpenicillin versus *E. coli*, *S. aureus* and *Pseudomonas aeruginosa*.

The compounds of TAble II have the formula:

Table II.

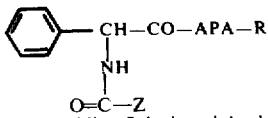

In Vivo Spectrum of Guanidino-Substituted Acyl Derivatives of α-Aminobenzylpenicillin Versus *Escherichia coli* 266. % Protection at 50 mg./kg. in Mice Via Subcutaneous Route

| Z | R=H % Protection | R=POM* % Protection |
|---|---|---|
| $CH_2NH—C(NH)NH_2$ | 100 | 90 |
| $CH_2N(CH_3)—C(NH)NH_2$ | 60 | 70 |
| $CH_2CH_2NH—C(NH)NH_2$ | 70 | 100 |
| $CH_2—NH\underset{NH}{\overset{N}{<}}$ | 90 | |

TABLE I.

In Vitro Spectra of Guanidino-Substituted Acyl Derivatives of α-Aminobenzylpenicillin Against Certain Gram-negative organisms (MIC'S)

| Z | E.coli 266 | Pseudo.aeruginosa 104 | | 173 | 490 | vul-garis A059 | Proteus rett-geri B006 | mira-bilis C015 | mira-bilis C020 | Serr-atia mar-cesens A001 | R* |
|---|---|---|---|---|---|---|---|---|---|---|---|
| $CH_2NH—C(NH)NH_2$ | 1.56 | 1.56 | 1.56 | 1.56 | 1.56 | 12.5 | 1.56 | 1.56 | 6.25 | | H |
| $CH_2N(CH_3)—C(NH)NH_2$ | 6.25 | 50 | 12.5 | 3.12 | 6.25 | 100 | 6.25 | 6.25 | 3.12 | | H |
| $CH_2CH_2NH—C(NH)NH_2$ | 3.12 | 6.25 | 3.12 | 3.12 | 3.12 | 50 | 0.78 | 12.5 | 6.25 | | H |
| $CH_2NH\underset{NH}{\overset{N}{<}}$ | 12.5 | 6.25 | 3.12 | 3.12 | 3.12 | 100 | 3.12 | 6.25 | 25 | | H |
| ⟨⟩-NH-C(NH)NH$_2$ | 3.12 | 0.78 | 0.78 | 0.78 | 6.25 | 25 | 3.12 | 12.5 | 3.12 | | H |
| ⟨⟩-NH-C(NH)NH$_2$ | 3.12 | 1.56 | 1.56 | 0.78 | 3.12 | 12.5 | 6.25 | 25 | 12.5 | | H |
| ⟨S⟩-NH-C(NH)NH$_2$ | 6.25 | 3.12 | 1.56 | 6.25 | 50 | 50 | 6.25 | 25 | 12.5 | | H |
| CH$_2$⟨⟩-NH-C(NH)NH$_2$ | 6.25 | 6.25 | 3.12 | 1.56 | 12.5 | — | 12.5 | — | 25 | | H |
| ⟨N⟩-C(NH)NH$_2$ | 6.25 | 12.5 | 6.25 | 1.56 | 6.25 | — | 3.12 | — | 6.25 | | H |
| $CH_2—NH—C(NH)NHCH_3$ | 1.56 | 1.56 | 3.12 | 0.78 | 3.12 | — | 1.56 | — | 3.12 | | H |
| $CH_2—N—C(NH)—NHCH_2CH_2$ | 6.25 | 12.5 | 12.5 | 3.12 | 6.25 | — | 3.12 | — | 12.5 | | H |
| $—NH—C(NH)NH_2$ | 3.1 | 2.5 | 1.5 | 1.5 | 1.56 | — | 0.78 | — | 6.25 | | H |
| $CH_2NH—C(NH)NH_2$ | 25 | — | — | 0.78 | — | — | 50 | — | — | | POM |
| $CH_2N(CH_3)—C(NH)NH_2$ | 12.5 | — | — | 3.12 | — | — | 12.5 | — | — | | POM |
| $CH_2CH_2NH—C(NH)NH_2$ | 6.25 | — | — | 6.25 | — | — | 0.39 | — | — | | POM |
| Ampicillin | 3.1 | 200 | 200 | 0.78 | 6 | — | 1.5 | — | 200 | | H |

*POM = hydrochloride salt of pivaloyloxymethyl ester.

Additionally, the compounds of this invention are active versus gram-positive and gram-negative bacteria in vivo via the parenteral route of administration in animals, including man. Their in vivo activity in animals, including man, by the oral route of administration is more limited as regards susceptible organisms. Nev-

⟨⟩-NH-C(NH)NH$_2$   10

⟨⟩-NH-C(NH)NH$_2$   60

⟨S⟩-NH-C(NH)NH$_2$   50

Table II.-continued

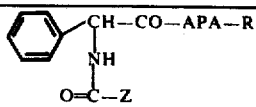

In Vivo Spectrum of Guanidino-Substituted Acyl Derivatives of α-Aminobenzylpenicillin Versus *Escherichia coli* 266. % Protection at 50 mg./kg. in Mice Via Subcutaneous Route

| Z | R=H % Protection | R=POM* % Protection |
|---|---|---|
| CH₂-⟨⟩-NH-C(NH)NH₂ | 20 | |
| ⟨N⟩-C(NH)NH₂ | 80 | |
| CH₃NH—C(NH)—NHCH₃ | 100 | |
| CH₂—N—C(NH)—NHCH₂CH₂<br>—NH—C(NH)NH₂ | 100 | |
| Ampicillin | 100 | |

*POM = hydrochloride salt of pivaloyloxymethyl ester.

TABLE III.

Comparative PD₅₀ Values (mg./kg.) of Compounds A, B and D-α-Aminobenzylpenicillin Versus Acute Systemic Infections in Mice

| | | Compound | | |
|---|---|---|---|---|
| Organism | Route | A | B | D-α-amino-benzylpenicillin |
| E. coli | subcutaneous | 6 | 15 ± 6.5 | 27 ± 9 |
| E. coli | oral | 50 | >200 | 25 ± 13 |
| S. aureus | subcutaneous | 13 ± 3.9 | 18 ± 9.8 | 0.67 ± 0.4 |
| S. aureus | oral | 68 | >100 | 2.5 ± 0.7 |
| P. aeruginosa | subcutaneous | 41 ± 13 | 41 ± 13 | >200 |
| P. aeruginosa | oral | >200 | >200 | >200 |

The dual in vivo activity of 6-[D-2-phenyl-2-(guanidinoacetamido)acetamido]penicillanic acid [A] is in surprising contrast to the in vivo activity of the structurally related prior art compound 6-[D-2-phenyl-2-(3-guanylueido)acetamido]penicillanic acid [B] which lacksoral activity against *E. coli* and *S, aureus*. Futher, compounds A and B are active against *Pseudomonas aeruginosa* whereas D-α-aminobenzylpenicillin is inactive.

The acute systemic infections in mice were produced by the intraperitoneal inoculation of standardized cultures suspended in 5% hog gastric mucin. Treatment with the drugs was initiated 0.5 hours after inoculation of the infecting organism. A second dose was administered four hours later. The PD₅₀ values were calculated after a hold period of four days.

Many of the compounds of this invention possess interesting and advantageous pharmacokinetic properties not found in structurally related penicillanic acid derivatives. For example, 6-[D-2-phenyl-2-(guanidinoacetamido)acetamido]penicillanic acid is shown by parenteral pharmacokinetic studies in dogs to be clearly superior to the structurally related compound 6-[D-2-phenyl-2-(3-guanylureido)acetamido]-penicillanic acid in terms of blood levels of drug and in total urinary recovery of drug (Tables IV and V).

Table IV.

Comparative Average Serum Levels of 6-[D-2-Phenyl-2-(Guanidino-acetamido)Acetamido]Penicillanic [A] and 6-[D-2-Phenyl-2-(3-Guanylureido)Acetamido]Penicillanic Acid [B] in Dogs for a Single Intramuscular Dose of 25 mg./kg.

| Com-pound | No. of Dogs | Serum Levels (mcg./ml.) at Indicated Hours | | | | | | |
|---|---|---|---|---|---|---|---|---|
| | | 0 | 0.5 | 1 | 2 | 3 | 4 | 6 |
| A | 4 | 0 | 30.4 | 26.2 | 10.3 | 2.1 | 0 | 0 |
| B | 4 | 0 | 3.5 | 3.6 | 0.8 | 0 | 0 | 0 |

Serum samples from a dog administered a single intramuscular dose of 50 mcg./kg. of [A] gave serum concentrations of 78 and 48 mcg./ml. at one and two hours post administration.

TABLE V.

Comparative Average Urine Levels of 6-[D-2-Phenyl-2-(Guanidino-acetamido)Acetamido]Penicillanic Acid [A] and 6-[D-2-Phenyl-2-(3-Guanylureido)Acetamido]Penicillanic Acid [B] in Dogs Given a single Intramuscular Dose of 25 mg./kg.

| Com-pound | % of Dose Recovered | Concentrations in Urine (mcg./ml.) at Indicated Hours | | | | | | |
|---|---|---|---|---|---|---|---|---|
| | | 0 | 0.5 | 1 | 2 | 3 | 4 | 5 |
| A | 35.4 | 0 | 366 | 710 | 1016 | 554 | 219 | 130 |
| B | 9.5 | 0 | 26.8 | 165 | 205 | 203 | 142 | 102 |

The oral and parenteral dosage levels for the herein described compounds are, in general, on the order of from about 25–200 mg./kg. of body weight per day and from about 10–100 mg./kg. of body weight per day, respectively. For topical application, the dosage level is on the order of from about 10–200 mg./kg./day.

When used for the purposes described herein, the valuable products of this invention can be used alone or in admixture with other antibiotics or in combination with a pharmaceutical carrier selected on the basis of the chosen route of administration and standard pharmaceutical practic. For example, they may be administered orally in the form of tablets containing such excipients as starch, milk sugar, certain types of clay, etc., or in capsules alone or in admixture with the same or equivalent excipients. They may also be administered orally in the form of elixirs or oral suspensions which may contain flavoring or coloring agents, or be injected parenterally, that is, for example, intramuscularly or subcutaneously. For parenteral administration they are best used in the form of a sterile solution or suspension which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

Many of the penicillin ester compounds of this invention exhibit improved absorption on oral administration over that produced by the corresponding free acid or alkali metal salt forms. They, therefore, represent convenient and effective dosage forms of the novel penicillins of formula I above.

Further, many of the esters, especially the acyloxy(lower alkyl) esters described herein, although inactive or of relatively low activity against gram-negative organisms per se are, when administered orally to animals, including man, metabolized to the parent acid which has a wide spectrum of activity against gram-positive and gram-negative bacteria. They thus serve as sources of the parent compounds since they are biologically converted in vivo to said compounds. The rate of metabolic conversion of such esters to the parent acid occurs at such a rate as to provide an effective and prolonged concentration of the parent acid in the animal body. In effect, such esters act as depot sources for the parent acid. Especially useful in this respect are the acyloxy(lower alkyl) esters such as the benzoyloxymethyl-, acetoxymethyl-, acetoxyethyl-, pivaloyloxymethyl- and α-ethylbutyryloxymethyl esters.

Compounds of formula I in which X is X' wherein X' is, or contains, a substituted phenylene group wherein the substituent is at least one of lower alkyl, lower alkoxy, chloro, bromo, fluoro, trifluoromethyl or di(-lower alkyl)-amino; and those wherein X represents pyrrolyl; as well as those compounds of formula I wherein at least one of $R_3$, $R_4$, $R_5$ or $R_6$ is alkenyl of from two to six carbon atoms are also effective antibacterial agents in the same manner as are the products embraced by formula I above. Such products are prepared by the methods described herein using as acylating agents the appropriate α-amino substituted acylamidopenicillanic acid of formula II and the appropriate guanidino substituted acid derivative of formula III wherein the X and $R_3$ – $R_6$ variables are as disclosed above.

Additionally, analogous derivatives of 7-aminocephalosporanic acid, desacetoxy 7-aminocephalosporanic acid, desacetyl 7-aminocephalosporanic acid and tertiary amine derivatives of 7-aminocephalosporanic acid wherein the 3-acetoxy group is displaced by a tertiary amine function as antibacterial agents against both gram-positive and gram-negative bacteria. Such derivatives are used in substantially the same manner as are the 6-[α-( -guanidinoalkanoylamido)acylamido]-penicillanic acid derivatives described herein. They are prepared by acylation of the appropriate 7-[(α-amino-substituted)acylamido]-cephalosporanic acid compounds of formula V below with a reactive functional derivative of an appropriate guanidino substituted acid of formula III according to methods described herein.

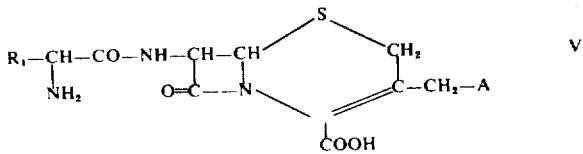

In formula V, $R_1$ is as defined above and A is selected from the group consisting of hydrogen, hydroxy, acetoxy and tertiary amino. Representative of the tertiary amino groups which displace the acetoxy moiety are pyridine, imidazole, benzimidazole, pyrimidine and substituted derivatives of these amines and tri(alkyl)amines (especially those wherein the alkyl group contains from one to six carbon atoms). Additionally, other amines and other nucleophiles such as sulfur compounds (e.g., thiourea, xanthates, dithiocarbamates, mercaptoimidazole, alkyl and aryl mercaptans), and carbon nucleophiles (e.g., indole, N-methyl-indole, resorcinol) also displace the 3-acetoxy group to afford compounds of formula V wherein A represents the nucleophilic agent to afford effective broad-spectrum antibacterial agents. Compounds of formula V, or methods for their preparation, are described in the literature; U.S. Pat. 3,560,489; U.S. Pat. 3,575,969; French Pat. 2,032,408; J. Antibiot. Ser. A 19 (6), 243–9 (1966); Cocket et al., J. Chem. Soc., 5015–5031 (1969).

Products of formula V can also, of course, be prepared by acylation of 7-aminocephalosporanic acid or related derivatives thereof (desacetoxy, desacetyl, tertiary amine betaine) with an acid of formula IV. However, availability of starting materials renders the above described methods the preferred routes.

The 6-[α-( -guanidinoalkanoylamido)acylamido]-penicillanic acids of formula I and the analogous derivatives of 7-aminocephalosporanic acid, its desacetyl-, desacetoxy- and tertiary amine derivatives, wherein $R_3$ and $R_4$ when taken together with the guanidine moiety to which they are attached form an imidazolo group, and those wherein one or more of the nitrogen atoms of the guanidino moiety is substituted with lower alkyl, phenyl or benzyl, are also active antibacterial agents. Such compounds, useful for the same purpose and in the same manner as compounds of formula I, are prepared from appropriate reactants by methods described herein.

The necessary reactants,

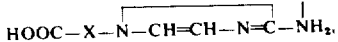

are prepared by reacting 2-aminoimidazole with the ethyl ester of the appropriate bromo acid BR—X—COOC$_2$H$_5$ in a 1 to 1 molar ratio in ethanol at the reflux temperature. The product is recovered by concentration of the reaction mixture followed by trituration of the residue with acetone. The product is then

EXAMPLE I

6-[D-2-Phenyl-2-(Guanidinoacetamido)Acetamido]-Penicillanic Acid

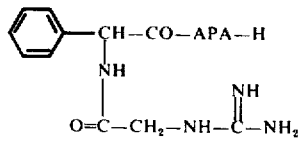

To a stirred suspension of the triethylamine salt of D-α-aminobenzylpenicillin (1.35 g., 3 mM) in dry N,N-dimethylformamide (12 ml.) at room temperature under a nitrogen atmosphere was added triethylamine (0.42 ml., 3 mM). The mixture was cooled to 0° C., guanidinoacetyl chloride hydrochloride (0.510 g., 3 mM) added and stirring continued for 30 minutes. The cooling bath was removed and the temperature allowed to reach room temperature. Thin layer chromatography in sodium acetate (7 ml. of 0.2M)-acetone (30 ml.) showed an estimated 40% of unreacted D-α-aminobenzylpenicillin still present. The mixture was cooled to 0° C. and triethylamine (0.21 ml., 1.5 mM) and guanidinoacetyl chloride hydrochloride (0.255 g., 1.5 mM) added. Stirring and cooling at 0° C. continued for 15 minutes, followed by 30 minutes at room temperature.

The reaction mixture was filtered and the filtrate poured into diethyl ether (300 ml.). The light pink solid which precipitates is collected by filtration and dried in vacuo (2.3 g.). The crude product is suspended in methylene chloride (100 ml.), triethylamine (2.5 ml.) added and the mixture stirred for one-half hour at room temperature, and then filtered to give the title product (0.987 g.; 67% yield).

Guanidinoacetyl Chloride Hydrochloride

The hydrochloride salt of guanidinoacetyl chloride was prepared by stirring a suspension of guanidinoacetic acid hydrochloride (1.53 g., 0.01M), methylene chloride (50 ml.) and phosphorous pentachloride (2.08 g., 0.01M) at room temperature under a nitrogen atmosphere overnight. The product, a white solid, was collected by filtration under nitrogen (0.893 g., 47.2% yield).

EXAMPLE II

6-[D-2-Phenyl-2-(Guanidinoacetamido)Acetamido]-Penicillanic Acid, Pivaloyloxymethyl Ester, Hydrochloride

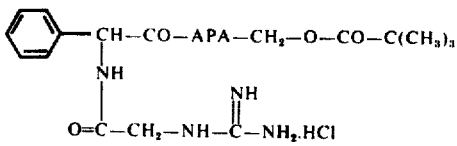

Triethylamine (0.42 ml., 3 mM) was added to a solution of D-α-aminobenzylpenicillin, pivaloyloxymethyl ester, hydrochloride (750 mg., 1.5 mM) in dry methylene chloride (12 ml.) under nitrogen and the mixture stirred and cooled to 0° C. Guanidinoacetyl chloride hydrochloride (202 mg., 1.8 mM) was added and the mixture stirred at 0° C. for 15 minutes, followed by 30 minutes at room temperature. The reaction mixture was again cooled to 0° C., guanidinoacetyl chloride hydrochloride (202 mg., 1.8 mM) added and the mixture then stirred at room temperature for one hour. It was again cooled to 0° C., guanidinoacetyl chloride hydrochloride (85 mg., 0.48 mM) added, the cooling bath removed, and the temperature allowed to rise to room temperature. After stirring for one-half hour, it was evaporated in vacuo and the residue (1.65 g.) triturated with ethyl acetate (100 ml.). The solid was filtered off, the filtrate washed with saturated sodium chloride solution, dried and evaporated in vacuo to give the product (490 mg., 55% yield).

Repetition of this procedure but replacing D-α-aminobenzylpenicillin, pivaloyloxymethyl ester, hydrochloride with equimolar amounts of the appropriate acyloxyalkyl ester produces compounds of the formula

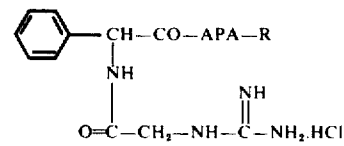

wherein R is
—CH$_2$—O—CO—CH(C$_2$H$_5$)$_2$
—CH$_2$—O—-aminobenzylpenicillin, C$_3$H$_7$
—CH(CH$_3$)—O—CO—CH$_3$
—CH$_2$—O—CO—C$_6$H$_5$
—CH$_2$—O—CO—(4-ClC$_6$H$_4$)
—CH$_2$—O—CO—(2-CH$_3$C$_6$H$_4$)
—CH(C$_2$H$_5$)—O—CO—C$_6$H$_5$
—CH$_2$—O—CO—[4-(n-C$_4$H$_9$)C$_6$H$_4$]
—CH$_2$—O—CO—(3-BrC$_6$H$_4$)
—CH$_2$—O—CO—(2-CF$_3$C$_6$H$_4$)
—CH$_2$—O—CO—(2-CH$_3$OC$_6$H$_4$)
—CH$_2$—O—CO—(3-FC$_6$H$_4$)

EXAMPLE III

6-[D-2-Phenyl-2-(2-Guanidinopropionamido)Acetamido]Penicillanic Acid, Pivaloyloxymethyl Ester, Hydrochloride

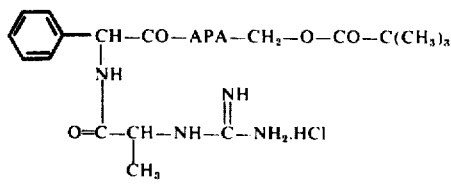

Triethylamine (0.42 ml., 3 mM) was added to a solution of D-α-aminobenzylpenicillin, pivaloyloxymethyl ester, hydrochloride (1.5 g., 3 mM) in dry N,N-dimethylformamide (9 ml.) at room temperature followed by dicyclohexylcarbodiimide (618 mg., 3 mM) and N-amidinoalanine hydrochloride (500 mg., 3 mM). The thick reaction mixture was stirred for one hour at room temperature after which the dicyclohexylcarbodiimide and N-amidinoalanine additions were repeated and stirring continued for an additional hour. The reaction mixture was filtered and the filtrate poured into diethyl ether (1 liter). The product precipitated and was collected by filtration and air dried. Yield = 2.4 g. of light yellow powder.

It was purified by dissolution in ethyl acetate and thorough washing of the solution with saturated aqueous sodium chloride. After drying with anhydrous sodium sulfate the ethyl acetate was removed under reduced pressure to give 1.5 g. of product.

N-Amidinoalanine Hydrochloride

N-amidinoalanine (3 g.) was suspended in diethyl ether (50 ml.) and excess hydrogen chloride gas bubbled in over a 15-minute period. The product was collected as a white gum by decantation of the diethyl ether.

EXAMPLE IV

6-[D-2-Phenyl-2-(Guanidinopropionamido)Acetamido]Penicillanic Acid

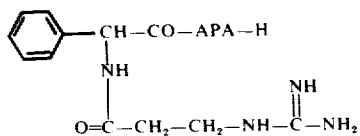

A mixture of D-α-aminobenzylpenicillin, triethylamine salt, (1.35 g., 3 mM) and triethylamine (0.42 ml., 3 mM) in dry N,N-dimethylformamide (17 ml.) was stirred under a nitrogen atmosphere and cooled to 0° C. Guanidinopropionyl chloride hydrochloride (745 mg., 3 mM) was added and the reaction mixture stirred for one-half hour at 0° C., followed by one hour at room temperature. The mixture was cooled to 0° C. and triethylamine (0.14 ml., 1 mM) and guanidinopropionyl chloride hydrochloride (186 mg., 1 mM) added. Stirring at 0° C. was continued for one-half hour followed by one hour at room temperature. The mixture was then filtered and the clear filtrate poured into diethyl ether (300 ml.). The light pink precipitate which formed was collected by filtration and dried in vacuo (1.6 g.). The dried solid was suspended in methylene chloride (125 ml.), triethylamine (2 ml.) added and the mixture stirred for one hour at room temperature. The light pink product was filtered off, washed with methylene chloride and dried in vacuo (1.1 g., 80% yield).

Guanidinopropionyl Chloride Hydrochloride

Guanidinopropionic acid was converted to the title compound according to the procedure given in Example I for making guanidinoacetyl chloride hydrochloride. The guanidinopropionic acid hydrochloride reactant was prepared from guanidinopropionic acid by bubbling hydrogen chloride gas into a suspension of the acid in diethyl ether. The white crystalline product was collected by filtration.

EXAMPLE V

6-[D-2-Phenyl-2-(Guanidinopropionamido)Acetamido]Penicillanic Acid, Pivaloyloxymethyl Ester, Hydrochloride

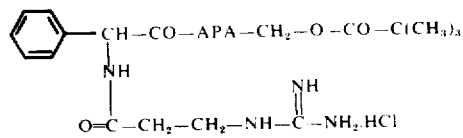

A solution of D-α-aminobenzylpenicillin, pivaloyloxymethyl ester, hydrochloride (1.5 g., 3 mM) in dry methylene chloride (45 ml.) was treated with triethylamine (0.42 ml., 3 mM), stirred and cooled to 0° C. Guanidinopropionyl chloride hydrochloride (560 mg., 3 mM) was added and the reaction mixture stirred at 0° C. for one hour. Triethylamine (0.14 ml., 1 mM) and guanidinopropionyl chloride hydrochloride (186 mg., 1 mM) were added and the mixture stirred at 0° C. for one hour. The addition of one millimole of each of triethylamine and acid chloride was repeated, followed by an additional hour of stirring at 0° C. One-half millimole of each of triethylamine (0.07 ml.) and acid chloride (93 mg.) were then added, and stirring continued at 0° C. for one hour. The reaction mixture was filtered and the filtrate evaporated under reduced pressure to give a white gummy residue. The residue was triturated with ethyl acetate (200 ml.), filtered and the filtrate washed with saturated aqueous sodium chloride (3 × 20 ml.), dried (Na$_2$SO$_4$) and evaporated under reduced pressure to give the title product as a white powder (1.1 g., 63.5% yield).

EXAMPLE VI

6-[D-2-Phenyl-2-(4-Guanidinobutyramido)Acetamido]Penicillanic Acid, Pivaloyloxymethyl Ester, Hydrochloride

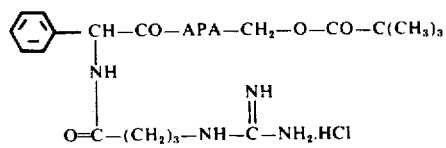

Triethylamine (0.28 ml., 2 mM) was added to a solution of the hydrochloride salt of D-α-aminobenzylpenicillin, pivaloyloxymethyl ester (1.0 g., 2 mM) in dry N,N-dimethylformamide (6 ml.) under a nitrogen atmosphere at room temperature. Dicyclohexylcarbodiimide (412 mg., 2 mM) was then added, the mixture stirred for three minutes, and 4-guanidinobutyric acid hydrochloride (362 mg., 2 mM) added. The thick reaction mixture was stirred at room temperature for 2.5 hours, at the end of which one equivalent of each of dicyclohexylcarbodiimide (412 mg., 2 mM) and 4-guanidinobutyric acid hydrochloride (362 mg., 2 mM) was added. Stirring was continued for an additional four hours after which the mixture was filtered and the filtrate poured into diethyl ether (300 ml.). The ether was decanted from the pale yellow solid which was then stirred for one more hour in a fresh volume of diethyl ether (300 ml.). The solid was collected and dried (1.16 g.).

The dried solid was stirred in methylene chloride (50 ml.) at room temperature for one-half hour, the suspension filtered and the filtrate evaporated to give 1.1 g. of product (88%).

EXAMPLE VII

6-{D-2-Phenyl-2-[(1-Methyl-guanidino)Acetamido]Acetamido}-Penicillanic Acid

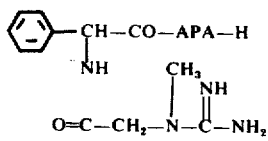

To a mixture of D-α-aminobenzylpenicillin, triethylamine salt, (1.35 g., 3 mM) and triethylamine (0.42 ml., 3 mM) in dry N,N-dimethylformamide (17 ml.) at 0° C. under an atmosphere of nitrogen was added (1-methylguanidino)acetyl chloride hydrochloride (600 mg., 3.2 mM) and the reaction mixture stirred at 0° C. for 15 minutes, followed by 1.5 hours at room temperature. The mixture was re-cooled to 0° C., an additional quantity of (1-methylguanidino)acetyl chloride hydrochloride (300 mg., 1.6 mM) added and stirring continued at 0° C. for 15 minutes followed by 1.5 hours at room temperature. The reaction mixture was again cooled to 0° C. and 1.6 mM of each of triethylamine (0.22 ml.) and (1-methylguanidino)acetyl chloride hydrochloride (300 mg.) was added. Stirring was continued at 0° C. for 15 minutes, followed by two hours at room temperature. The mixture was filtered and the filtrate slowly poured into diethyl ether (300 ml.) to precipitate a pink powder (1.6 g.). The powder was collected by filtration, dried and triturated in methylene chloride (125 ml.). Triethylamine (2 ml.) was added and the slurry stirred at room temperature for one hour and filtered. The filter cake is washed with methylene chloride and dried. Yield = 830 mg. (60%).

(1-Methylguanidino)Acetyl Chloride Hydrochloride

Creatine (5 g.) was suspended in diethyl ether (150 ml.) and hydrogen chloride gas bubbled in for one hour. The temperature was held at room temperature by external cooling. The precipitate was filtered off and air dried.

Creatine hydrochloride (1.85 g., 0.01 mole) in methylene chloride (50 ml.) was treated with phosphorous pentachloride (2.06 g., 0.01 mole) at room temperature. The mixture was stirred overnight at room temperature and the acid chloride product filtered off, washed with methylene chloride and dried.

EXAMPLE VIII

6-{D-2-Phenyl-2-[(1-Methyl-guanidino)Acetamido]Acetamido}-Penicillanic Acid, Pivaloyloxymethyl Ester, Hydrochloride

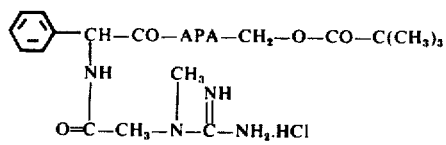

To a stirred solution of D-α-aminobenzylpenicillin, pivaloyloxymethyl ester, hydrochloride (1.5 g., 3 mM) in dry methylene chloride (50 ml.) was added triethylamine (0.42 ml., 3 mM). The mixture was cooled to 0° C., (1-methylguanidino)acetyl chloride hydrochloride (560 mg., 3 mM) added and stirring continued at 0° C. for 15 minutes, followed by one hour at room temperature. The reaction mixture was cooled to 0° C. and 3 millimoles of each of triethylamine and acid chloride added. The mixture was stirred at room temperature for one hour, re-cooled to 0° C. and acid chloride (280 mg., 1.5 mM) added. It was stirred for one hour at room temperature, again cooled to 0° C. and additional acid chloride (140 mg., 0.75 mM) added. The mixture was warmed to room temperature and stirred for 45 minutes. It was filtered, the filter cake washed with methylene chloride, and the combined filtrate and wash solutions evaporated under reduced pressure. The residue was triturated with ethyl acetate (125 ml.) and the solid filtered off. The filtrate was washed with saturated salt solution (3 × 20 ml.), dried (Na$_2$SO$_4$) and evaporated in vacuo to give 1.16 g. of product (67%).

EXAMPLE IX

6-{D-2-Phenyl-2-[(3-Methyl-guanidino)Acetamido]Acetamido}-penicillanic Acid, Pivaloyloxymethyl Ester, Hydrochloride

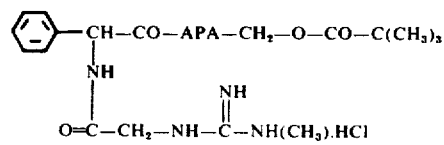

The procedure of Example VI was repeated but using (3-methylguanidino)acetic acid hydrochloride in place of 4-guanidinobutyric acid hydrochloride.

Thus, from 3 millimoles of pivaloyloxymethyl ester of D-α-aminobenzylpenicillin hydrochloride, 3-millimoles of triethylamine and 6 millimoles of each of dicyclohexyl carbodiimide and (3-methylguanidino)acetic acid hydrochloride in 40 ml. of dry N,N-dimethylformamide, an almost quantitative yield of product was obtained.

2-Methylguanidino Acetic Acid

N,N-dimethylisothiourea hydroiodide (9.5 g., 0.041 mole) was added portionwise to a stirred solution of glycine (4.45 g., 0.0595 mole) in concentrated ammonium hydroxide (40 ml.) at room temperature. The reaction was stirred overnight and the product recovered by filtration as white crystals: 3.0 g., m.p. 230° C. (dec.).

Repetition of this procedure but replacing the (2-methylquanidino)acetic acid hydrochloride used therein with an equimolar amount of:

(3-phenylguanidino)acetic acid
(3-n-butylguanidino)acetic acid
(1-ethylguanidino)acetic acid
3-guanidinobutyric acid
2-guanidinobutyric acid
3-guanidinopropionic acid
(2,3-dimethylguanidino)acetic acid
2-guandidinopropionic acid
5-guanidinovaleric acid
3-guandidino-2-methylpropionic acid
2-(β-carboxyethylamino)-2-imidazoline 2-[(carboxymethyl)methylamino]-2-imidazoline
2-(α-carboxypropylamino)-2-imidazoline
2-(carboxymethylamino)-2-(1,4,5,6-tetrahydropyrimidine)

2-(ε-carboxypentylamino)-2-imidazoline affords the following penicillanic acid pivaloyloxymethyl ester hydrochlorides. For convenience, only the 6-position substituents are listed:

6-{D-2-phenyl-2-[(3-phenyl-guanidino)acetamido]acetamido}
6-{D-2-phenyl-2-[(3-n-butyl-gaunidino)acetamido]acetamido}
6-{D-2-phenyl-2-[(1-ethyl-gaunidino)acetamido]acetamido}
6-[D-2-(3guanidinobutyramido)acetamido]
6-[D-2-phenyl-2-(2-guanidinobutyramido)acetamido]
6-[D-2-phenyl-2-(3-guanidinopropionamido)acetamido]
6-{D-2-phenyl-2-[(2,3-dimethylguanidino)acetamido]acetamido}
6-[D-2-phenyl-2-(2-guanidinopropionamido)acetamido]
6-[D-2-phenyl-2-(5-guanidinovalerylamido)acetamido]
6-[D-2-phenyl-2-(3-guanidino-2-methylpropionamido)acetamido]
6-{D-2-[3-(2-imidazolinylamino)propionamido]acetamido}
6-{D-2-phenyl-2-[(2-imidazolinyl)methylaminoacetamido]acetamido}
6-{D-2-phenyl-2-[2-(2-imidazolinylamino)butyramido]acetamido}
6-{D-2-phenyl-2-[(1,4,5,6-tetrahydro-2-pyrimidinyl)aminoacetamido]acetamido}
6-{D-2-phenyl-2-[6-(2-imidazolinyl)aminohexanoylamido]acetamido}

EXAMPLE X

6-[D-2-Phenyl-2-(2-Imidazolinylaminoacetamido)Acetamido]Penicillanic Acid

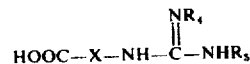

The procedure of Example VII was repeated but using N-(2-imidazolinyl)glycyl chloride hydrochloride in place of (1-methylguanidino)acetyl chloride as reactant.

Thus, D-α-aminobenzylpenicillin triethylamine salt (1.35 g., 3mM), triethylamine (0.77 ml., 5.5 mM) and N-(2-mid chloride hydrochloride (1.08 g., 5.5 mM) in dry N,N-dimethylformamide (15 ml.) gave 915 mg. (64.5%) of product.

The acid chloride and triethylamine were added in three portions as in Example VII but at the rate of 3.0, 1.5 and 1.0 millimoles per addition.

N-(2-Imidazolinyl)Glycyl Chloride Hydrochloride

This reactant was prepared from N-(2-imidazolinyl)glycine hydrochloride according to the procedure in Example VII for preparing (1-methylguanidino)acetyl chloride hydrochloride.

Repetition of this procedure but using the appropriate α-aminoacylpenicillin and the appropriate cyclic guanidino acid of the formula

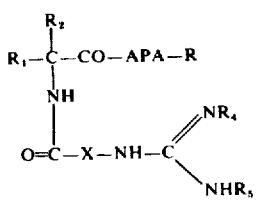

wherein $R_4$ and $R_5$ together with the guanyl residue to which they are attached represent 2-imidazolyl, 2-(2-imidazolinyl), 2-(1,4,5,6-tetrahydropyrimidinyl) and 2-pyrimidinyl, provides the following compounds:

| $R_1$ | $R_2$ | X | R | $-C(NR_4)-NHR_5$ |
|---|---|---|---|---|
| $C_6H_5$ | H | $CH_2$ | H | 2—Im |
| $C_6H_5$ | H | $CH_2$ | H | THP |
| $C_6H_5$ | H | $CH_2$ | H | PYR |
| $C_6H_5$ | H | $CHC_2H_5$ | H | Im |
| $C_6H_5$ | H | $(CH_2)_3$ | $CH_2OCOCH_3$ | THP |
| $C_6H_5$ | H | $(CH_2)_2$ | H | PYR |
| $C_3H_7$ | H | | H | PYR |
| $3-BrC_6H_4$ | H | $1,3-C_6H_4$ | H | 2—Im |
| $4-IC_6H_4$ | H | $1,4-C_6H_4$ | H | 2—Im |
| $C_6H_5$ | H | $1,4-CH_2OC_6H_4$ | H | Im |
| $2-NO_2-C_6H_4$ | H | $1,4-CH=CHC_6H_4$ | H | PYR |
| $4-CF_3C_6H_4$ | H | $(CH_2)_4$ | H | THP |
| $2-(CH_3)_2NHC_6H_4$ | H | $(CH_2)_2$ | H | THP |
| $4-H_2NSO_2C_6H_4$ | H | $CH=CH-CH_2$ | $CH_2OCOC_2H_5$ | THP |
| $4-t-C_4H_9C_6H_4$ | H | $1,4-C_6H_{10}$ | H | Im |
| $2,3,6-(CH_3)_3C_6H_2$ | H | $CHCH_3$ | $CH(CH_3)OCOC_2H_5$ | THP |
| $C_6H_{11}$ | H | $CH_2$ | H | Im |
| $C_3H_5$ | H | $1,4-C_6H_4$ | H | THP |
| H | H | $CH_2$ | H | 2—Im |
| H | $CH_3$ | $1,4-C_6H_4$ | H | THP |
| $C_2H_5$ | H | $(CH_2)_5$ | H | 2—Im |
| $C_5H_{11}$ | H | $CH_2$ | H | PYR |
| 1-naphthyl | H | $CH_2$ | H | Im |

-continued

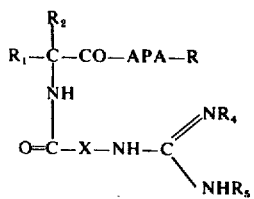

| R₁ | R₂ | X | R | —C(NR₄)—NHR₅* |
|---|---|---|---|---|
| 3-thienyl | H | CH₂ | CH₂OCOC₂H₅ | Im |
| 3-thienyl | H | CH₂ | H | THP |
| 2-thienyl | H | 1,3—C₆H₄ | H | PYR |
| 2-furyl | H | (CH₂)₃ | H | 2—Im |
| 3-indolymethyl | H | CH₂ | H | THP |
| CH₃S(CH₂)₄ | H | (CH₂)₃ | H | PYR |
| C₂H₅ | C₂H₅ | (CH₂)₇ | H | Im |
|  | —(CH₂)₂— | CH₂ | H | Im |
|  | —(CH₂)₃— | CH₂ | H | THP |
|  | —(CH₂)₄— | (CH₂)₂ | H | PYR |
|  | —(CH₂)₅ | 1,4—C₆H₄ | CH₂OCOC(CH₃)₃ | Im |
| C₆H₅ | CH₃ | CH₂ | H | 2—Im |
| C₆H₅ | C₂H₅ | CH=CH—CH₂ | H | PYR |
| 3-thienyl | H | CH=CH—CH₂ | H | Im |
| 3-thienyl | H | 1,4—CH=CHC₆H₄ | H | Im |
| 3-thienyl | H | 1,4—CH₂C₆H₄ | H | THP |
| 3-indolylmethyl | H | 1,3—CH₂C₆H₄ | H | THP |
| C₆H₅CH₂CH₂ | H | 1,4—CH₂OC₆H₄ | H | THP |
| 4—HOC₆H₄ | H | CH₂ | H | Im |
| 4—HOC₆H₄ | H | CH₂ | H | THP |
| 4—HOC₆H₄ | H | 1,4—C₆H₄ | H | Im |
| 4—HOC₆H₄ | H | 1,4—CH₂C₆H₄ | H | Im |
| 3—HOC₆H₄ | H | CHCH₃ | H | THP |
| 2—HOC₆H₄ | H | 1,4—C₆H₁₀ | H | 2—Im |
| 4—HOC₆H₄ | H | CH₂ | H | PYR |
| 4—ClC₆H₄ | H | CH₂ | H | PYR |
| 3—FC₆H₄ | H | CH₂CH₂ | H | Im |
| 1,4—cyclohexadienyl | H | CH₂ | H | Im |
| 1,4—cyclohexadienyl | H | 1,4—CH₂C₆H₄ | H | Im |
| 1,4—Cyclohexadienyl | H | 1,4—C₆H₄ | H | THP |
| 1,4—cyclohexadienyl | H | 1,4—C₆H₁₀ | H | PYR |

For those compounds wherein R is an ester group, the work-up of procedure V is used.
* Im = 2-imidazolyl
2-Im = 2-(2-imidazolinyl)
THP = 2-(1,4,5,6-tetrahydropyrimidinyl)
PYR = 2-pyrimidinyl

EXAMPLE XI

6-[D-2-Phenyl-2-(4-Guanidinobenzamido)Acetamido]Penicillanic Acid

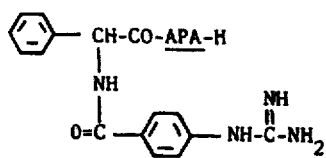

4-Guanidinobenzoyl chloride hydrochloride (585 mg., 2.5 mM) was added to a stirred mixture of D-α-aminobenzylpenicillin trihydrate (1.15 g., 2.85 mM) and triethylamine (0.35 ml., 2.5 mM) in dry N,N-dimethylformamide (10 ml.) at 0° C. and under an atmosphere of nitrogen. The reaction mixture was allowed to warm to room temperature by removing the cooling bath. Stirring was continued at room temperature for three hours. The mixture was filtered, the filtrate poured into diethyl ether (800 ml.) and the resulting precipitate collected by filtration and dried (2.0 g.). The crude product was suspended in methylene chloride (75 ml.), triethylamine (2 ml.) added, and the mixture stirred for one hour. The product was filtered off, washed with methylene chloride and dried, 1.07 g. (84.5% yield).

4-Guanidinobenzoyl Chloride Hydrochloride

A suspension of 4-guanidinobenzoic acid (1 6.) in water (25 ml.) was adjusted to pH 1.0 with 6N hydrochloric acid and then warmed to 50° C. The clear solution which resulted was cooled and the white crystalline hydrochloride salt of 4-guanidinobenzoic acid filtered off, washed thoroughly with diethyl ether and dried: 500 mg.; m.p. 270° C.

A mixture of the hydrochloride salt thus prepared (1.2 g.) and thionyl chloride (50 ml.) was refluxed for 10.5 hours (care being taken to exclude moisture) and then allowed to stand overnight at room temperature. The title product was recovered as a white powder by evaporation of the excess thionyl chloride.

In accordance with the above acylation procedure, the 4-guanidinobenzoyl chloride hydrochloride is replaced by an equimolar amount of the acid chloride hydrochlorides of the following acids:
2-phenyl-4-guanidinobenzoic acid
2-phenyl-4-guanidinomethylbenzoic acid
4-guanidinomethylphenylacetic acid
α-guanidino-octanoic acid
α-guanidino-β-phenylpropionic acid
1-guanyl-4-piperidinocarboxylic acid
to give the penicillanic acids listed below. Only the 6-position substituents are given for convenience:
6-[D-2-phenyl-2-(2-phenyl-4-guanidinobenzamido)acetamido]

6-[D-2-phenyl-2-(2-phenyl-4-guanidinomethylbenzamido)acetamido]

6-[D-2-phenyl-2-(4-guanidinomethylphenylacetamido)acetamido]

6-[D-2-phenyl-2(α-guanidino-octanoylamido)acetamido]

6-[D-2-phenyl-2-(α-guanidino-β-phenylpropionamido)acetamido]

6-[D-2-phenyl-2-(1-guanyl-4-piperidylcarboxamido)acetamido]

EXAMPLE XII

6-[D-2-Phenyl-2-(3-Guanidinobenzamido)Acetamido]Penicillanic Acid

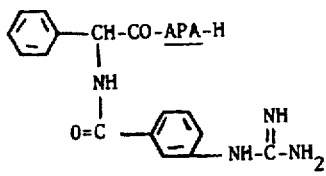

To a stirred mixture of D-α-aminobenzylpenicillin trihydrate (810 mg., 2 mM) and triethylamine (0.56 ml., 4 mM) in dry N,N-dimethylformamide (15 ml.) cooled to −30° C. was added a solution of 3-guanidinobenzoyl chloride hydrochloride (560 mg., 2.4 mM) in dry N,N-dimethylformamide (5 ml.) over a five-minute period. The cooling bath was removed and the temperature allowed to rise to room temperature. The mixture was stirred for forty minutes and then worked up according to the method of Example XI. Yield = 974 mg. (95%) as a white powder.

3-Guanidinobenzoyl Chloride Hydrochloride

A mixture of benzoylcyanamid (1.62 g.), m-aminobenzoic acid (1.37 g.) and ethanol (5 ml.) was heated to 100° C., the ethanol being allowed to evaporate off. When most of the ethanol had distilled off, additional ethanol (10 ml.) was added and heating continued until about one-third volume remained. The mixture was then cooled, filtered and the solid product washed first with ethanol, then with ether, and dried (2.4 g.).

The 3-(3-benzoylguanidino)benzoic acid (1.4 g.) thus prepared was refluxed in 1N sodium hydroxide (16 ml.) for one hour. The reaction mixture was cooled, adjusted to pH 6 and the resulting precipitate filtered off. It was washed successively with water, acetone and ether, and dried (0.558 g. of 3-guanidinobenzoic acid).

A mixture of thionyl chloride (5 ml.) and 3-guanidinobenzoic acid was refluxed for 40 minutes and then evaporated to dryness in vacuo to give the acid chloride.

EXAMPLE XIII

6-D-2-Phenyl-2-(4-Guanidinocyclohexylcarboxamido)Acetamido Penicillanic Acid Hydrochloride

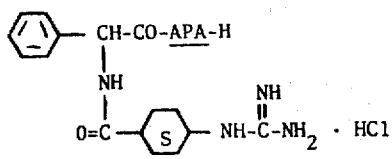

Triethylamine (0.38 ml., 2.66 mM) was added to a stirred suspension of D-α-aminobenzylpenicillin trihydrate (0.536 g., 1.33 mM) in dry N,N-dimethylformamide (5 ml.). The mixture was cooled to 0° C. and the acid chloride of 4-guanidinocyclohexylcarboxylic acid hydrochloride (0.319 g., 1.33 mM) added. The mixture was warmed to room temperature over a three-hour period. Methylene chloride (65 ml.) was added and the resulting yellow precipitate filtered off, washed with diethylether and dried (0.664 g.). The solid was suspended in methylene chloride (20 ml.), triethylamine (1 ml.) added and the mixture stirred for one hour. The suspension was filtered and the product dried in vacuo (0.461 g., 53% yield).

Acid Chloride of 4-Guanidinocyclohexylcarboxylic Acid Hydrochloride

A mixture of 4-aminocyclohexylcarboxylic acid (5.26 g., 0.037 M), concentrated ammonium hydroxide (24 mls.) and 2-methyl-2-thiopseudourea sulfate (6.7 g., 0.024 M) was stirred at room temperature for 21 hours. The mixture was cooled in an ice bath and the product, 4-guanidinocyclohexylcarboxylic acid, filtered off, triturated with acetone and dried (0.407 g.).

It was converted to the hydrochloride salt by bubbling hydrogen chloride gas through a suspension of the guanidino acid in ether (40 ml.) for 15 minutes. The salt was filtered off and converted to the acid chloride hydrochloride according to the procedure given in Example XI.

EXAMPLE XIV

6-{D-2-Phenyl-2-[(4-Guanidinophenyl)Acetamido]Acetamido}Penicillanic Acid

The procedure of Example XII was repeated but using 4-guanidinophenyl acetyl chloride -Guandinocinnomoylamido]as acylating agent in place of 3-guanidinobenzoyl chloride hydrochloride and an initial temperature of −70° C. rather than −30° C. Yield = 2.65 g. (78.5%) of product as a white powder from D-α-aminobenzylpenicillin trihydrate (2.62 g., 6.45 mM), triethylamine (1.8 ml., 12.9 mM) and acid chloride (1.6 g., 6.45 mM) in dry N,N-dimethylformamide (35 ml.).

EXAMPLE XV

6-{D-2-Phenyl-2-[(4-Guanidinocinnamoylamido]Acetamido}Penicillanic Acid

To a solution of D- α-aminobenzylpenicillin trihydrate (0.921 g., 2.28 mM) and triethylamine (0.64 ml., 4.56 mM) in dry N,N-dimethylformamide (23 ml.) at 0° C. was added a solution of 4-guandidinocinnamoyl chloride hydrochloride (0.593 g., 2.28 mM) in dry N,N-dimethylformamide (5 ml.). The mixture was stirred at 0° C. for five minutes and the temperature then allowed to rise to room temperature. Stirring was continued for one-half hour after which the mixture was filtered and the filtrate poured into diethyl ether (800 ml.). The precipitate was collected and dried (1.58 g.). It was suspended in methylene chloride (30 ml.), triethylamine (0.5 ml.) added and the mixture stirred for one hour. The product was collected by filtration of the slurry, washed with methylene chloride and dried. 1.111 g. (90.7% yield).

The 4-guanidinocinnamoyl chloride hydrochloride was prepared from 4-aminocinnamic acid according to the procedure of Example XII for preparing 3-guanidinobenzoyl chloride hydrochloride.

EXAMPLE XVI

6-[D-2-Phenyl-2-(4-Guanidinocyclohexylcarboxamido)Acetamido]Penicillanic Acid

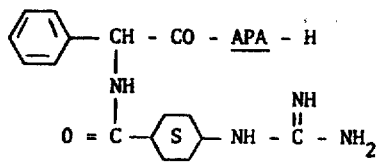

To a solution of 4-guanidinocyclohexane carboxylic acid (370 mg., 2mM) in N,N-dimethylformamide (10 ml.) was added dicyclohexylcarbodiimide (454 mg., 2.2 mM) in N,N-dimethylformamide (5 ml.) followed by a solution of D-α-aminobenzylpenicillin trihydrate (810 mg., 2 mM) in water-N,N-dimethylformamide (12 ml. of 1:1) containing sufficient sodium bicarbonate to give a pH of 7.0. The mixture was stirred for two hours at room temperature and then filtered to remove dicyclohexylurea. The filtrate was poured into acetone (2 liters) with stirring and the product recovered by filtration and dried.

Repetition of this procedure but replacing 4-guanidinocyclohexane carboxylic acid by an equivalent amount of:

2-guanidinopalmitic acid
2-(-(-guanidinophenoxy)butyric acid
4-guanidinophenoxyacetic acid
4-guanidinomethylphenoxyacetic acid
2-(4-guanidinomethylphenoxy)propionic acid
2-(4-guanidinomethylphenoxy)propionic acid
4-(1-methylguanidino)crotonic acid
2-guanidinocyclohexane carboxylic acid
4-guanidinocrotonic acid
4-(3-n-butylguanidino)crotonic acid
3-guanidinocyclohexane carboxylic acid
2-guanidinocyclopentane carboxylic acid
3-guanidinocyclopentane carboxylic acid
3-guanidinocyclobutane carboxylic acid
1-amidino-2-pyrrolidine carboxylic acid
2-imino-4-imidazolidine carboxylic acid
1-guanidinocyclobutane carboxylic acid
1-guanidino-2-methylcyclobutane carboxylic acid
1-guanidinocyclopentane carboxylic acid
1-guanidinocyclopropane carboxylic acid
1-guanidinocyclohexane carboxylic acid
1-guanidino-3-fluorocyclohexane carboxylic acid
1-guanidion-2-propoxycyclohexane carboxylic acid
1-guanidino-3-nitrocyclohexane carboxylic acid
1-guanidinocycloheptane carboxylic acid
1-guanidino-2-ethylcycloheptane carboxylic acid
1-guanidinocyclo-octane carboxylic acid respectively, afford the corresponding penicillanic acid derivatives.

EXAMPLE XVII

Following the procedures of Examples, I, II, VII, IX, XI and XVI, the penicillanic acids listed below are prepared from appropriate 6-(α-aminoacylamido)-penicillanic acids [$R_1R_2C(NH_2)$-CO-APA-R] and guanidino-substituted acids or acid halides thereof [Z-CO-X-N($R_3$)-C(=$NR_4$)-$NR_5R_6$]:

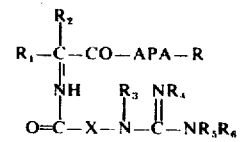

| $R_1$ | $R_2$ | $R_3$ | $R_4$ | $R_5$ | $R_6$ | R | X | Proc. Ex. |
|---|---|---|---|---|---|---|---|---|
| $C_6H_5$ | $CH_3$ | H | $C_2H_5$ | H | $CH_3$ | H | $CH_2$ | I |
| $C_6H_5$ | $CH_3$ | H | $C_6H_5$ | H | n—$C_4H_9$ | H | $CH_2$ | I |
| $C_6H_5$ | H | H | $C_7H_7$ | $C_2H_5$ | H | H | $CH_2$ | I |
| H | H | H | H | H | H | H | $CH_2$ | I |
| H | H | H | H | H | H | $CH_2OCOCH(C_2H_5)_2$ | $CH_2$ | II |
| H | H | H | $CH_3$ | $CH_3$ | $CH_3$ | H | $1,4-C_6H_4$ | I |
| i—$C_3H_7$ | H | H | H | H | H | $CH(CH_3)OCOC_2H_5$ | $CH_2$ | II |
| n—$C_4H_9$ | H | H | H | H | $CH_3$ | $CH_2OCO(4-CF_3C_6H_4)$ | $CHCH_3$ | II |
| n—$C_6H_{13}$ | H | H | $CH_3$ | H | H | H | $CH_2$ | I |
| $C_7H_7$ | H | H | H | H | H | H | $CH_2$ | I |
| 1-naphthyl | H | H | H | H | H | H | $(CH_2)_2$ | XI |
| 1-naphthyl | H | $CH_3$ | H | H | H | $CH_2OCOC_6H_5$ | $1,4-CH_2OC_6H_4$ | II |
| 2-furyl | H | H | H | H | H | H | $CH_2$ | I |
| 2-thienyl | H | H | H | H | $CH_3$ | H | $CH_2$ | I |
| 2-thienyl | H | H | $C_6H_5$ | H | $CH_3$ | $CH_2OCOC(CH_3)_3$ | $1,4-C_6H_{10}$ | II |
| 3-thienyl | H | H | H | H | H | H | $CH_2$ | XI |
| 3-thienyl | H | H | $CH_3$ | H | $C_7H_7$ | H | $(CH_2)_4$ | XI |
| 3-thienyl | H | H | H | $CH_3$ | $CH(CH_3)OCOCH_3$ | H | $1,4-C_6H_4$ | II |
| 3-indolylmethyl | H | H | H | H | H | H | $CH_2$ | I |
| $CH_3S(CH_2)_3$ | H | H | H | n—$C_4H_9$ | H | H | $CH_2CH=CH$ | I |
| $CH_3S(CH_2)_6$ | H | H | H | H | H | H | $1,4-CH_2C_6H_4$ | I |
| $C_2H_5S(CH_2)_2$ | H | H | H | H | $C_2H_5$ | H | $1,4-CH_2OC_6H_4$ | I |
| 4—$ClC_6H_4$ | H | H | H | H | H | H | $CH_2-CH=CH$ | I |

-continued

| R₁ | R₂ | R₃ | R₄ | R₅ | R₆ | R | X | Proc. Ex. |
|---|---|---|---|---|---|---|---|---|
| C₇H₇ | H | H | CH₃ | CH₃ | H | H | (CH₂)₂ | I |
| C₇H₇ | H | H | C₂H₅ | CH₃ | H | H | CH₂ | I |
| C₆H₅CH₂CH₂ | H | H | H | H | CH₃ | H | CH₂ | I |
| C₆H₅CH₂CH₂ | H | H | CH₃ | H | H | H | 1,4—C₆H₄CH₂ | VII |
| C₆H₅ | H | CH₃ | H | H | H | H | CHCH₃ | VII |
| C₆H₁₁ | H | CH₃ | H | H | H | H | CH₂ | VII |
| 2—ClC₆H₄ | H | H | H | H | C₂H₅ | H | CH₂ | I |
| 2—ClC₆H₄ | H | H | H | H | H | H | (CH₂)₃ | I |
| 3—ClC₆H₄ | H | H | H | CH₃ | H | H | 1,4—C₆H₄ | I |
| 4—ClC₆H₄ | H | H | H | H | H | H | 1,3—C₆H₄ | I |
| 4—ClC₆H₄ | H | H | H | H | H | CH₂OCOC(CH₃)₃ | CH₂ | II |
| 4—ClC₆H₄ | H | H | H | H | H | H | CHC₆H₁₃ | I |
| 4—ClC₆H₄ | H | H | H | H | H | H | CHC₂H₅ | I |
| 3—IC₆H₄ | H | H | H | H | H | H | 1,4—C₆H₁₀ | I |
| 4—IC₆H₄ | H | CH₃ | H | CH₃ | H | H | (CH₂)₄ | XI |
| 3—CH₃C₆H₄ | H | H | H | H | CH₃ | H | (CH₂)₆ | XI |
| 2—CH₃OC₆H₄ | H | H | H | H | H | H | CH₂ | XI |
| 4—HOC₆H₄ | H | H | H | H | H | CH₂OCOC₆H₅ | CHCH₃ | II |
| 4—HOC₆H₄ | H | H | H | CH₃ | C₂H₅ | CH₂OCOCH₃ | 1,4—C₆H₄CH₂ | II |
| 4—t—C₄H₉C₆H₄ | H | H | H | H | H | CH(CH₃)OCOCH₃ | (CH₂)₃ | II |
| 4—H₂NSO₂C₆H₄ | H | H | CH₃ | CH₃ | H | CH₂OCO(4—ClC₆H₄) | CH₂ | II |
| 3—FC₆H₄ | H | H | CH₃ | C₂H₅ | H | H | CH₂ | I |
| 2—NO₂C₆H₄ | H | H | CH₃ | H | H | CH₂OCO(2—CH₃C₆H₄) | (CH₂)₄ | II |
| 2—NO₂C₆H₄ | H | H | H | H | n—C₄H₉ | CH₃OCOCH(C₂H₅)₂ | 1,4—CH=CHC₆H₄ | II |
| 4—CF₃C₆H₄ | H | H | H | H | n—C₃H₇ | CH₂OCOCH(CH₃)₂ | CH₂ | II |
| 2—CH₃CONHC₆H₄ | H | CH₃ | H | CH₃ | C₂H₅ | H | CH₂ | I |
| 4—(C₂H₅)₂NC₆H₄ | H | CH₃ | H | CH₃ | H | H | (CH₂)₂ | I |
| 4—CH₃OC₆H₄ | H | CH₃ | CH₃ | CH₃ | H | H | CH₂ | I |
| 2—(CH₃)₂NC₆H₄ | H | H | H | H | H | H | 1,4—CH=CHC₆H₄ | II |
| 2—(CH₃)₂NC₆H₄ | H | H | H | H | i—C₃H₇ | CH₂OCOC₂H₅ | 1,3—C₆H₁₀ | II |
| 4—n—C₄H₉OC₆H₄ | H | H | C₂H₅ | H | C₂H₅ | CH(CH₃)OCOCH₃ | 1,3—C₆H₁₀ | II |
| 4—n—C₄H₉OC₆H₄ | H | H | H | H | H | H | CH₂ | I |
| C₆H₅ | CH₃ | H | H | H | H | H | 1,4—C₆H₄ | I |
| C₆H₅ | CH₃ | H | H | H | H | H | CH₂ | I |
| C₆H₅ | CH₃ | H | C₃H₇ | H | H | H | CH₂ | I |
| C₆H₅ | CH₃ | H | C₆H₅ | H | CH₃ | H | 1,4—CH=CHC₆H₄ | I |
| —CH₂—CH₂— | | H | H | H | H | H | 1,3—C₆H₄ | I |
| —CH₂—CH₂— | | H | H | H | H | H | 1,4—C₆H₁₀ | II |
| —CH₂—CH₂—CH₂— | | H | H | H | H | CH₂OCOC₂H₅ | (CH₂)₄ | |
| —CH₂—CH₂—CH₂— | | H | H | CH₃ | H | H | 1,4—CH₂OC₆H₄ | II |
| —(CH₂)₅— | | H | H | H | H | CH₂OCOC(CH₃)₃ | CHCH₃ | |
| —(CH₂)₅— | | H | H | H | H | H | 1,4—C₆H₄CH₂ | I |
| —(CH₂)₅— | | H | H | i—C₄H₉ | CH₃ | H | CH₂ | I |
| —(CH₂)₅— | | H | C₆H₅ | H | H | H | 1,3—C₆H₄ | I |
| —(CH₂)₅— | | H | H | H | H | H | 1,4—C₆H₁₀ | I |
| CH₃ | CH₃ | H | H | H | H | H | CH₂—CH=CH— | XI |
| C₂H₅ | CH₃ | H | H | H | H | H | —CH₂—CH=λ | XI |
| C₆H₁₁ | CH₃ | H | H | H | H | H | CH—(CH₂)₇ | XI |
| C₂H₅ | C₂H₅ | H | H | CH₃ | H | H | 1,2—C₆H₁₀ | XVI |
| C₆H₅ | CH₃ | H | H | H | C₆H₅ | H | 1,1—C₃H₄ | XVI |
| 4—CH₃C₆H₄ | H | H | H | H | H | H | 1,3—C₄H₆ | XVI |
| H | H | H | H | H | H | H | 1,2—C₅H₈ | XVI |
| CH₃ | CH₃ | H | CH₃ | CH₃ | H | H | 1,3—C₆H₁₀ | XVI |
| n—C₆H₁₃ | H | H | H | H | n—C₃H₇ | H | 1,3—C₆H₁₀ | II |
| n—C₆H₁₃ | H | H | H | H | n—C₃H₇ | CH₂OCOCH₃ | CH₂ | I |
| C₆H₁₁ | H | H | H | H | H | H | 1,4—C₆H₄ | I |
| C₆H₁₁ | H | H | H | H | C₆H₅ | H | (CH₂)₃ | I |
| C₆H₁₁ | H | H | CH₃ | H | H | H | CH₂ | II |
| C₆H₁₁ | H | H | CH₃ | H | C₇H₇ | CH(CH₃)OCOC₂H₅ | CH₂ | II |
| C₃H₅ | H | H | H | H | CH₃ | CH₂OCOCH(C₂H₅)₂ | CH₂ | II |
| C₃H₅ | CH₃ | H | H | H | H | H | 1,4—C₆H₁₀ | I |
| C₃H₅ | CH₃ | H | H | H | H | H | 1,1—C₃H₄ | I |
| C₆H₅ | CH₃ | H | H | H | H | H | 1,1—C₆H₆ | II |
| H | H | H | H | H | H | n—C₄H₉ | CH₂OCOCH(CH₃)₂ | 1,1—C₃H₄ | II |
| C₆H₅ | CH₃ | H | H | H | H | H | 1,2—C₆H₁₀ | I |
| 4—CH₃C₆H₄ | H | H | H | H | H | H | 1,3—C₆H₁₀ | I |
| C₆H₅ | H | H | H | H | H | H | 1,1—C₇H₁₂ | I |
| 2—ClC₆H₄ | H | H | CH₃ | H | CH₃ | H | 1,1—C₈H₁₄ | I |
| C₃H₅ | CH₃ | H | H | CH₃ | H | H | CH₂ | II |
| 3—HOC₆H₄ | H | H | H | H | H | H | (CH₂)₂ | |
| 3—HOC₆H₄ | H | H | H | H | CH₃ | CH₂OCOC₂H₅ | CH₂ | |
| 2—HOC₆H₄ | H | H | H | H | H | H | CH₂ | |
| 1,4-cyclohexadienyl | H | H | H | H | H | H | 1,4—C₆H₄CH₂— | I * |
| 2,6—(CH₃)₂—4—(PrO)C₆H₂ | H | H | H | H | H | CH(CH₃)OCOCH₃ | (CH₂)₃ | II * |
| 2,4—(C₂H₅O)₂—5—PrC₆H₂ | H | CH₃ | H | H | H | H | 1,4—C₆H₄ | VII |
| C₆H₅ | H | CH₃ | H | H | H | H | 1,4—C₆H₁₀ | VII |
| C₆H₁₁ | CH₃ | CH₃ | H | H | H | H | CH₂ | VII |
| C₆H₅ | CH₃ | CH₃ | H | H | H | H | (CH₂)₃ | VII |
| 3-thienyl | H | CH₃ | H | H | H | H | CH₂ | VII |
| 3-thienyl | H | CH₃ | H | H | H | CH₂OCOC(CH₃)₃ | CH₂ | II |
| 2-thienyl | H | CH₃ | H | H | H | H | CH₂ | VII |
| 4—ClC₆H₄ | H | CH₃ | H | H | H | H | CH₂ | VII |
| C₆H₅ | CH₃ | H | H | H | H | H | CH₂ | VII |
| C₆H₅ | H | n—C₃H₇ | H | H | H | H | CH₂ | VII |
| 2—CH₃OC₆H₄ | H | n—C₄H₉ | H | H | H | H | CH₂ | VII |
| C₆H₅ | H | H | C₆H₅ | H | H | H | CH₂ | VII |
| 1-naphthyl | H | H | C₆H₅ | H | H | H | CH₂ | I |
| C₆H₅ | H | H | CH₃ | CH₃ | H | H | CH₂ | I |
| 3-thienyl | H | H | CH₃ | CH₃ | H | H | CH₂ | I |
| —(CH₂)₆— | | H | CH₃ | H | H | H | | |

-continued

| R₁ | R₂ | R₃ | R₄ | R₅ | R₆ | R | X | Proc. Ex. |
|---|---|---|---|---|---|---|---|---|
| C₆H₅ | H | CH₃ | H | C₆H₅ | H | H | CH₂ | I |
| 3-thienyl | H | CH₃ | H | C₆H₅ | H | H | CH₂ | I |
| H | H | CH₃ | H | CH₃ | H | H | CH₂ | I |
| C₂H₅ | CH₃ | CH₃ | H | C₆H₅ | H | H | CH₂ | I |
| 1,4-cyclohexadienyl | H | H | H | H | CH₃ | H | 1,4—C₆H₄ | I |
| 1,4-cyclohexadienyl | H | H | H | H | H | CH₂OCOCH₃ | CH₂ | II |

* Pr = n—C₃H₇

EXAMPLE XVIII

When in Example XI, the D-α-aminobenzylpenicillin trihydrate is replaced by equimolar amounts of the following α-aminoacylpenicillins:

aminomethyl-
α-aminoheptyl-
α-aminopentyl-
α-aminoisobutyl-
α-amino-o-chlorobenzyl-
α-amino-m-chlorobenzyl-
α-amino-p-chlorobenzyl-
α-amino-1,4-cyclohexadienylmethyl-
α-amino-4-hydroxybenzyl-
α-amino-4-iodobenzyl-
α-amino-3-fluorobenzyl-
α-amino-p-methoxybenzyl-
α-amino-2-nitrobenzyl-
α-amino-4-t-butylbenzyl-
α-amino-3-methylbenzyl-
α-amino-4-sulfamylbenzyl-
α-amino-1-naphthylmethyl-
α-amino-β-phenethyl-
α-amino-2-furylmethyl-
α-amino-2-thienylmethyl-
α-amino-3-thienylmethyl-
α-amino-3-indolylmethyl-
α-amino-γ-methylthiopropyl-
α-amino-γ-ethylthiopropyl-
α-aminocyclohexylmethyl-
α-aminocyclopentylmethyl-
α-amino-p-trifluorobenzyl-
α-amino-2-acetamidobenzyl-
1-aminocyclooctyl-
1-aminocyclohexyl-
1-aminocyclobutyl-
1-aminocyclopropyl-
1-aminocyclononyl-
α-amino-3-hydroxybenzyl
α-amino-4-diethylaminobenzyl
α-amino-3-bromobenzyl
α-amino-α-methylbenzyl respectively, the corresponding [guanidinoalkanoylamidoacylamido]penicillanic acids are produced.

EXAMPLE XIX

6-{D-2-Phenyl-2-[2-(2-Amino-4-Imidazolinylcarboxamido)]Acetamido}-Penicillanic Acid

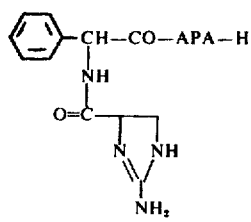

The hydrochloride salt of the acid chloride of 2-amino-2-imidazoline-4-carboxylic acid (450 mg., 2.5 mM was reacted with D-α-aminobenzylpenicillin trihydrate (1.15 g., 2.85 mM) according to the procedure of Example XI to give the title product.

The acid chloride of 2-amino-2-imidazoline-4-carboxylic acid was prepared from the hydrochloride salt by treatment with thionyl chloride according to the method of Example XI.

Repetition of this procedure but using 2-amino-2-(1,4,5,6-tetrahydropyrimidine)-5-carboxylic acid hydrochloride in place of 2-amino-2-imidazoline-4-carboxylic acid hydrochloride affords 6-{D-2-Phenyl-2-[2-(2-amino-5-(1,4,5,6-tetrahydropyrimidinylcarboxamido)]acetamido}penicillanic acid.

Repetition of this procedure but replacing D-α-aminobenzylpenicillin trihydrate by the α-aminoacylpenicillins listed in Example XVIII produces the corresponding penicillins.

EXAMPLE XX

6-[D-2-Phenyl-2-(1-Guanyl-4-Piperidylcarboxamido)-Acetamido]Penicillanic Acid

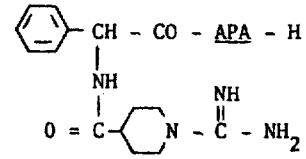

The procedure of Example XII was repeated but using D-α-aminobenzylpenicillin trihydrate (3.22 g., 8 mM) in N,N-dimethylformamide (30 ml.), triethylamine (224 ml., 1.6 mM, and the acid chloride of 1-guanyl-4-piperidinecarboxylic acid hydrochloride (2.26 g., 10 mM) in N,N-dimethylformamide (10 ml.). The product was obtained as a light pink powder, 3.4 g., (84%).

1-Guanyl-4-Piperidinecarboxylic Acid Chloride

4-Piperidinecarboxylic acid (6.45 g., 0.05 mole) was dissolved in concentrated ammonium hydroxide (40 ml.) and S-methylisothiourea (6.95 g., 0.05 mole) added. The resulting solution was stirred thoroughly and then allowed to stand overnight at room temperature. The product, which precipitated, was filtered off, washed with ethanol and dried; 4.41 g. (52.4% yield).

The acid chloride was prepared by stirring a mixture of equimolar amounts of the N-guanyl substituted acid and phosphorous pentachloride in methylene chloride overnight at room temperature under an atmosphere of nitrogen. The methylene chloride was decanted from the oil which was washed twice with methylene chloride and then dried in vacuo to a white gum.

Repetition of this procedure but replacing D-α-aminobenzylpenicillin trihydrate by an equivalent amount of D-α-amino-3-methylbenzylpenicillin
D-α-amino-4-chlorobenzylpenicillin
D-α-amino-1,4-cyclohexadienylmethylpenicillin
D-α-amino-3-bromobenzylpenicillin
D-α-amino-4-sulfamylbenzylpenicillin
D-α-amino-4-diethylaminobenzylpenicillin
d-α-amino-4-trifluoromethylbenzylpenicillin
D-α-amino-2-acetamidobenzylpenicillin
aminomethylpenicillin
α-aminoheptylpenicillin
α-aminocyclohexylmethylpenicillin
α-amino-2-thienylmethylpenicillin
α-amino-3-thienylmethylpenicillin
α-amino-2-furylmethylpenicillin
α-amino-β-(3-indolyl)ethylpenicillin
α-amino-β-phenethylpenicillin
α-amino-γ-phenylpropylpenicillin
α-amino-1-naphthylmethylpenicillin
α-amino-α-methylbenzylpenicillin
α-amino-sec-butylpenicillin
α-amino-ethylthioethylpenicillin
α-amino-ω-ethylthiopentylpenicillin
1-amino-1-cyclohexylpenicillin
1-amino-1-cyclobutylpenicillin
α-amino-4-hydroxybenzylpenicillin
α-amino-3-hydroxybenzylpenicillin
D-α-aminobenzylpenicillin, pivaloyloxymethyl ester
α-amino-3-thienylmethylpenicillin, acetoxymethyl ester
α-aminocyclohexylmethylpenicillin, 1-acetoxyethyl ester
α-amino-α-methylbenzylpenicillin, butyryloxymethyl ester
D-α-amino-4-sulfamylbenzylpenicillin, benzoyloxymethyl ester respectively, affords the corresponding penicillanic acid derivatives.

EXAMPLE XXI

6-[D-2-Phenyl-2-(1-Guanyl-2-Pyrrolidylcarboxamido)Acetamido]Penicillanic Acid

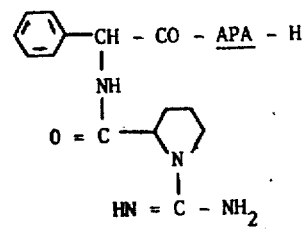

A suspension of dicyclohexylcarbodiimide (1.57 g., 7.7 mM), N-hydroxysuccinimide (0.875 g., 7.7 mM), 1-guanylproline (1.5 g., 7.7 mM) and N,N-dimethylformamide (50 ml.) was stirred for two hours at room temperature. The triethylamine salt of D-α-aminobenzylpenicillin (3.36 g., 7.7 mM) was added, the mixture stirred at room temperature for 2.5 hours, and then filtered. The filtrate was added to ether (1000 ml.), the mixture stirred, and the ether decanted from the gummy product. Methylene chloride (250 ml.) and triethylamine (2 ml.) were added to the gummy product, the mixture stirred for one-half hour, and the solid which formed recovered by filtration and dried over phosphorous pentoxide (1.9 g.).

By means of this procedure but using the appropriate α-aminoacylpenicillin and the appropriate 1-guanyl pyrrolidine carboxylic acid, the compounds listed below wherein R=H are prepared. Those compounds wherein R is an acyloxyalkyl group are prepared by the procedure of Example VI from the appropriate penicillin acyloxyalkyl ester.

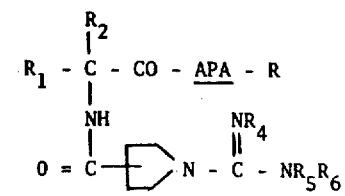

| $R_1$ | $R_2$ | $R_4$ | $R_5$ | $R_6$ | R | Isomer |
|---|---|---|---|---|---|---|
| $C_6H_5$ | H | H | H | H | H | 3 |
| $C_6H_5$ | H | H | $CH_3$ | H | $CH_2OCOCH(C_2H_5)_2$ | 2 |
| $C_6H_5$ | H | H | $CH_3$ | H | $CH_2OCOCH(C_2H_5)_2$ | 3 |
| $C_6H_5$ | H | $C_6H_5$ | H | $C_2H_5$ | H | 2 |
| $C_6H_5$ | H | $CH_3$ | H | $C_6H_5$ | H | 2 |
| $3-ClC_6H_4$ | H | H | H | H | H | 2 |
| $4-CF_3C_6H_4$ | H | $C_6H_5$ | $CH_3$ | H | H | 2 |
| $2-CH_3CONHC_6H_4$ | H | H | H | $C_6H_5$ | H | 3 |
| $2-NO_2C_6H_4$ | H | H | H | H | $CH(CH_3)OCOC_2H_5$ | 2 |
| $4-BrC_6H_4$ | H | H | H | $C_6H_5$ | H | 3 |
| $4-HOC_6H_4$ | H | H | H | H | H | 3 |
| $4-HOC_6H_4$ | H | H | $CH_3$ | H | $CH_2OCOC(CH_3)_3$ | 2 |
| $4-(C_2H_5)_2NC_6H_4$ | H | H | $CH_3$ | $CH_3$ | H | 2 |
| $C_7H_7$ | H | H | H | H | H | 2 |
| $C_6H_5CH_2CH_2$ | H | H | H | H | H | 3 |
| $4-(H_2NSO_2)C_6H_4$ | H | H | H | H | H | 3 |
| $C_5H_9$ | H | H | $C_2H_5$ | H | H | 2 |
| $C_5H_9$ | H | H | $C_2H_5$ | H | $CH_2OCO(-4-ClC_6H_4)$ | 2 |
|  | $-(CH_2)_3-$ | H | H | H | H | 2 |
|  | $-(CH_2)_5-$ | H | H | H | H | 3 |
|  | $-(CH_2)_4-$ | H | H | H | H | 2 |
| 3-thienyl | H | H | H | H | H | 2 |
| 3-thienyl | H | H | $CH_3$ | $CH_3$ | H | 2 |
| 2-thienyl | H | H | H | H | $CH(CH_3)OCOCH_3$ | 3 |
| 2-furyl | H | H | H | H | $CH(CH_3)OCOCH_3$ | 3 |
| 3-indolylmethyl | H | $CH_3$ | H | $C_6H_5$ | H | 2 |
| 1-naphthyl | H | $CH_3$ | H | $CH_3$ | H | 2 |
| $C_2H_5SCH_2CH_2$ | H | H | H | H | $CH_2OCOC_3H_7$ | 2 |

-continued

| $R_1$ | $R_2$ | $R_4$ | $R_5$ | $R_6$ | R | Isomer |
|---|---|---|---|---|---|---|
| H | H | H | H | H | H | 2 |
| H | H | H | H | H | $CH_2OCOCH(C_2H_5)_2$ | 2 |
| $CH_3$ | $CH_3$ | H | H | H | H | 3 |
| $C_2H_5$ | $CH_3$ | $CH_3$ | H | $CH_3$ | H | 3 |
| $C_6H_5$ | $CH_3$ | H | H | H | H | 2 |
| $C_3H_5$ | $CH_3$ | H | H | H | H | 2 |
| 4—$CH_3OC_6H_4$ | $CH_3$ | $CH_3$ | H | $C_7H_7$ | H | 2 |
| $C_6H_{11}$ | $CH_3$ | $C_7H_7$ | $C_2H_5$ | H | H | 3 |
| $C_6H_{11}$ | H | H | H | H | H | 2 |
| $C_6H_{13}$ | H | H | H | H | H | 2 |
| 1,4—cyclohexadienyl | H | H | H | H | H | 2 |
| 1,4—cyclohexadienyl | H | H | H | H | H | 3 |
| 2—$HOC_6H_4$ | H | H | H | $CH_3$ | H | 2 |

EXAMPLE XXII

6-[D-2-Phenyl-2-(3-Methylguanidino)Acetamido Acetamido]Penicillanic Acid

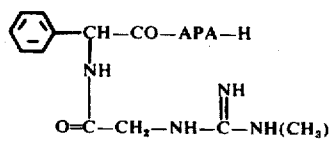

Repetition of the procedure of Example I but using 3-methylguanidinoacetyl chloride hydrochloride as acylating agent in place of α-guanidinophenylacetyl chloride afforded the title product. Thus, using 2.65 mM of each of D-α-aminobenzylpenicillin and 3-methylguanidinoacetyl chloride hydrochloride, 5.3 mM of triethylamine and 25 ml. of dimethylformamide, 755 mg. (62% yield) of product was obtained.

EXAMPLE XXIII

6-[D-2-Phenyl-2-(1-Guanyl-3-Piperidylcarboxamido)-Acetamido]Penicillanic Acid

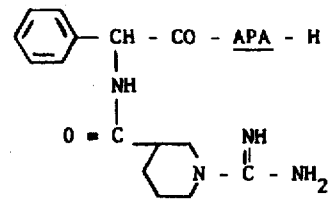

Following the procedure of Example I but using 1-guanyl-3-piperidine carboxylic acid hydrochloride as acylating agent in place of α-guanidinophenylacetyl chloride provides 482 mg. (48% yield) of the title product.

The above-named acylating agent is prepared from 3-piperidine carboxylic acid according to the procedure of Example XX for making 1-guanyl-4-piperidine carboxylic acid. Utilization of 2-piperidine carboxylic acid in place of the 4-isomer provides 1-guanyl-2-piperidine carboxylic acid.

The following penicillanic acid derivatives are prepared in like manner from appropriate reactants

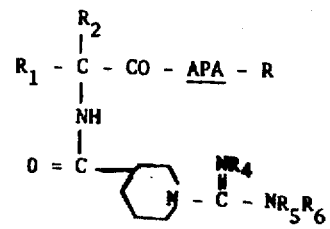

| $R_1$ | $R_2$ | $R_4$ | $R_5$ | $R_6$ | R | Isomer |
|---|---|---|---|---|---|---|
| $C_7H_7$ | H | H | H | H | H | 2 |
| $C_6H_5$ | H | H | $CH_3$ | H | H | 4 |
| $C_6H_5$ | H | H | $CH_3$ | $CH_3$ | H | 4 |
| $C_6H_5$ | H | $C_6H_5$ | $C_2H_5$ | H | H | 4 |
| 4—$CF_3C_6H_4$ | H | $CH_3$ | $C_2H_5$ | H | $CH(CH_3)OCOC_2H_5$ | 3 |
| 4—$CH_3OC_6H_4$ | H | $CH_3$ | $CH_3$ | H | H | 3 |
| 4—$HOC_6H_4$ | H | H | H | H | H | 3 |
| 4—$HOC_6H_4$ | H | H | H | H | H | 4 |
| 4—$NO_2C_6H_4$ | H | H | H | H | H | 3 |
| 4—$H_2NSO_2C_6H_4$ | H | H | $CH_3$ | H | H | 4 |
| 3—$BrC_6H_4$ | H | H | H | H | $CH(CH_3)OCOCH_3$ | 4 |
| 3-thienyl | H | H | H | H | H | 3 |
| 2-thienyl | H | H | H | H | H | 3 |
| indolylmethyl | H | H | H | H | H | 3 |
| 2-furyl | H | $CH_3$ | $CH_3$ | H | H | 2 |
| $C_6H_{11}$ | H | H | H | H | H | 3 |
| H | H | H | H | H | H | 3 |
| $CH_3$ | H | H | H | H | H | 4 |
| i—$C_3H_7$ | H | H | H | H | H | 3 |
| $C_6H_{13}$ | H | H | H | H | H | 3 |
|  | —$(CH_2)_5$— | H | H | H | H | 3 |
|  | —$(CH_2)_5$— | H | H | H | $CH_2OOC(CH_3)_3$ | 3 |
|  | —$(CH_2)_2$— | H | H | H | H | 3 |
|  | —$(CH_2)_6$— | H | H | H | H | 3 |
| $C_2H_5$ | $CH_3$ | H | H | H | H | 4 |
| $C_6H_5$ | $CH_3$ | H | $CH_3$ | H | H | 3 |
| 1-naphthyl | H | H | H | H | H | 2 |
| $CH_3$ | $CH_3$ | $C_6H_5$ | H | $CH_3$ | H | 3 |
| $C_2H_5S(CH_2)_2$ | H | H | H | H | $CH_2OCOC_6H_5$ | 3 |

| $R_1$ | $R_2$ | $R_4$ | $R_5$ | $R_6$ | R | Isomer |
|---|---|---|---|---|---|---|
| | | | | | -continued | |
| 1,4—cyclohexadienyl | H | H | H | H | H | 4 |
| 4—$(C_2H_5)_2NC_6H_4$ | H | H | H | $CH_3$ | H | 4 |
| 4—$ClC_6H_4$ | H | H | $CH_3$ | H | H | 3 |
| 1,4—cyclohexadineyl | H | H | H | H | $CH(CH_3)OCOCH_3$ | 4 |

The esters listed above are prepared from appropriate reactants by the procedure of Example VI.

EXAMPLE XXIV

6- D-2-Phenyl-2-[1-(2-Iminoimidazolidino)-]Acetamido -Penicillanic Acid

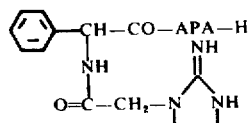

To a stirred solution of triethylamine (2.79 ml., 0.02 M) in dry N,N-dimethylformamide (100 ml.) was added d-α-aminobenzylpenicillin trihydrate (4.03 g., 0.01 M). When solution was complete, the reaction mixture was cooled to 0°C. and the acid chloride of 1-carboxymethyl-2-iminoimidazolidine hydrochloride (1.97 g., 0.01 M) added. The mixture was stirred at 0° C. for ten minutes followed by 1.5 hours at room temperature. It was then filtered and the filtrate poured into diethyl ether (2 liters). The solid which precipitated was filtered off under an atmosphere of nitrogen and then taken up in methylene chloride (250 ml.). Triethylamine (2.79 ml.) was added, the mixture stirred for one-half hour and then filtered under a nitrogen atmosphere. The product was dried in vacuo (2.4 g., 50.6% yield).

The acid chloride reactant was prepared from 1-carboxymethyl-2-iminoimidazolidine by the procedure of Example VII.

In like manner, the following compounds are prepared from the appropriate α-aminoacylpenicillin and the appropriate imidazolidine and hexahydropyrimidine reactants

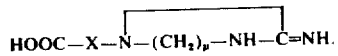

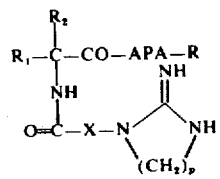

| $R_1$ | $R_2$ | X | R | p |
|---|---|---|---|---|
| $C_6H_5$ | H | $CH_2$ | H | 3 |
| $C_6H_5$ | H | $CH_2$ | $CH_2OCOC(CH_3)_3$ | 2 |
| $C_6H_5$ | H | $(CH_2)_5$ | H | 3 |
| 4—$BrC_6H_4$ | H | $CH_2$ | H | 2 |
| 4—$HOC_6H_4$ | H | $CH_2$ | H | 3 |
| 4—$HOC_6H_4$ | H | $CH_2CH_2$ | H | 2 |
| 3-thienyl | H | $CH_2$ | H | 2 |
| 3-thienyl | H | 1,4—$CH_2C_6H_4$ | H | 2 |
| 2-thienyl | H | $CH_2$ | H | 2 |
| 2-furyl | H | $CH_2$ | $CH_2OCOCH_3$ | 3 |
| 4—$(CH_3)_2NC_6H_4$ | H | $(CH_2)_5$ | H | 3 |
| $C_6H_5$ | H | $(CH_2)_5$ | H | 2 |
| $C_6H_5$ | H | $(CH_2)_7$ | H | 2 |
| $C_6H_5$ | H | $(CH_2)_3$ | H | 3 |
| $C_6H_{11}$ | H | 1,4—$C_6H_4$ | H | 2 |
| $C_6H_{11}$ | H | 1,4—$C_6H_{10}$ | H | 2 |
| $C_4H_7$ | H | 1,4—CH=$CHC_6H_4$ | H | 2 |
| $C_6H_5$ | H | 1,4—$C_6H_{10}$ | H | 3 |
| 4—$ClC_6H_4$ | H | 1,3—$C_6H_4$ | H | 3 |
| 4—$(C_2H_5O)C_6H_4$ | H | 1,4—$CH_2C_6H_4$ | H | 3 |
| $C_6H_5$ | H | 1,4—$CH_2C_6H_4$ | H | 3 |
| 4—$CH_3C_6H_4$ | H | CH=CH—$CH_2$ | H | 2 |
| $C_6H_5$ | H | 1,4—CH=$CHC_6H_4$ | H | 2 |
| 1,4—cyclohexadienyl | H | 1,4—$CH_2OC_6H_4$ | $CH(CH_3)OCOCH_3$ | 3 |
| $C_6H_5$ | H | $CH_2$ | H | 3 |
| | —$CH_2CH_2CH_2$— | $CH_2$ | H | 3 |
| | —$(CH_2)_5$— | $CHCH_3$ | H | 3 |
| | —$(CH_2)_4$— | $CH_2CH_2$ | H | 2 |
| | | $CH_2$ | $CH(CH_3)OCOC_2H_5$ | 3 |
| H | H | 1,4—$C_6H_4$ | H | 3 |
| H | H | $CH_2CH_2$ | H | 2 |
| $CH_3$ | H | 1,3—$C_6H_4$ | H | 3 |
| $C_2H_5$ | $CH_3$ | CH=CH—$CH_2$ | $CH_2 OCOC_6H_5$ | 3 |
| $C_6H_{13}$ | H | $CH_2$ | H | 2 |
| $C_2H_5SCH_2CH_2$ | H | $CH_2$ | H | 3 |
| 3—indolylmethyl | H | $(CH_2)_7$ | H | 2 |
| $C_7H_7$ | H | $CH_2$ | H | 2 |
| $C_6H_5$ | $CH_3$ | $CH_2$ | H | 3 |
| 1,4—cyclohexadienyl | H | $CH_2$ | H | 2 |
| 1,4—cyclohexadienyl | H | $CH_2$ | H | 3 |
| 1—naphthyl | H | $CHCH_3$ | H | 3 |
| $C_6H_5$ | $C_2H_5$ | $CH_2$ | H | 3 |
| 4—$H_2NSO_2C_6H_4$ | H | $CH_2$ | $CH_2OCO(4-ClC_6H_4)$ | 2 |
| 3-thienyl | H | 1,4—CH=CH—$C_6H_4$ | H | 3 |
| 3-thienyl | H | 1,3—CH=CH—$C_6H_4$ | H | 3 |
| 3-thienyl | H | 1,2—CH=CH—$C_6H_4$ | H | 3 |
| 3—$NO_2C_6H_4$ | H | 1,2—CH=CH—$C_6H_4$ | H | 2 |

-continued

| R₁ | R₂ | X | R | p |
|---|---|---|---|---|
| 4—HOC₆H₄ | H | 1,3—CH=CH—C₆H₄ | H | 2 |
| C₆H₅ | H | 1,4—CH₂OC₆H₄ | H | 2 |

The above listed esters are prepared from the appropriate acyloxyalkyl penicillin esters by the procedure of Example VI.

EXAMPLE XXV

6-{D-2-Phenyl-2-[2-(2-Amino-4-Imidazolinylcarboxamido)]Acetamido}Penicillanic Acid, Pivaloyloxymethyl Ester, Hydrochloride 2-Amino-2-imidazoline-4-carboxylic acid hydrochloride (3 mM) is reacted with D-α-aminobenzylpinicillin, pivaloyloxymethyl ester, hydrochloride according to the procedure of Example III to produce the title compound.

In like manner, the following compounds are prepared from appropriate acyloxyalkylpenicillin esters and 2-amino-2-imidazoline-4-carboxylic acid and 2-amino-2-(1,4,5,6-tetrahydropyrimidine)carboxylic acid hydrochlorides.

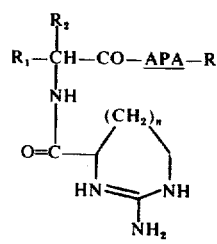

| R₁ | R₂ | R | n |
|---|---|---|---|
| C₆H₅ | H | CH₂OCOCH₃ | 1 |
| C₆H₅ | CH₃ | CH(CH₃)OCOCH₃ | 0 |
| 4—ClC₆H₄ | H | CH₂OCOC₆H₅ | 0 |
| 4—BrC₆H₄ | H | CH₂OCO—(3—CF₃C₆H₄) | |
| 3—C₂H₅C₆H₄ | H | CH₂OCO—n—C₄H₉ | 0 |
| 4—t—C₄H₉C₆H₄ | H | CH(CH₃)OCOC₂H₅ | 0 |
| 3—NO₂C₆H₄ | H | CH₂OCOCH(C₂H₅)₂ | 1 |
| 3—CF₃C₆H₄ | H | CH₂OCOC₂H₅ | 0 |
| 4—HOC₆H₄ | H | CH₂OCOC(CH₃)₃ | 1 |
| 2—HOC₆H₄ | H | CH₂OCOCH₃ | 1 |
| 4—(CH₃)₂NC₆H₄ | H | CH(CH₃)OCOCH₃ | 1 |
| 2—CH₃OC₆H₄ | H | CH₂OCO—(4—FC₆H₄) | 1 |
| 3—IC₆H₄ | H | CH₂OCO—i—C₃H₇ | 0 |
| 1,4—cyclohexadienyl | H | CH₂OCOC(CH₃)₃ | 0 |
| 1,4—cyclohexadienyl | H | CH(CH₃)OCOCH₃ | 1 |
| H | H | CH₂OCO-(4—CH₂OC₆H₄) | 0 |
| CH₃ | C₂H₅ | CH₂OCOC₂H₅ | 1 |
| C₆H₁₃ | H | CH₂OCO—(4—ClC₆H₄) | 1 |
| C₇H₇ | H | CH₂OCO—(3—BrC₆H₄) | 0 |
| C₆H₅CH₂CH₂ | H | CH₂OCO-(3—CH₃C₆H₄) | 1 |
| 2-thienyl | H | CH₂OCOCH(CH₃)₂ | 0 |
| 3-thienyl | H | CH₂OCOCH(C₂H₅)₂ | 0 |
| 2-furyl | H | CH₂OCOC₂H₅ | 1 |
| 3-indolylmethyl | H | CH(CH₃)OCOC₂H₅ | 1 |
| C₂H₅SCH₂CH₂ | H | CH₂OCOCH₃ | 0 |
| C₆H₁₁ | H | CH₂OCOC(CH₃)₃ | 0 |
| | —(CH₂)₃— | CH₂OCOCH(CH₃)₂ | 0 |
| | —(CH₂)₅— | CH₃OCOCH₃ | 0 |

EXAMPLE XXVI

6- D-2-Phenyl-2-[(3-Allyl-guanidino)Acetamido]Acetamido Penicillanic Acid
-Allylguandino)Acetyl

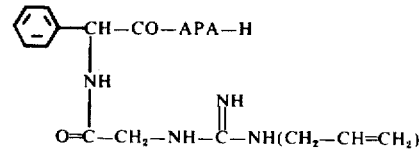

T D-α-aminobenzylpenicillin, triethylamine salt (7.02 g., 15.6 mM) and triethylamine (1.09 ml., 7.8 mM) in dry N,N-dimethylformamide (24 ml.) at 0° C. was added (3-allylguanidino)acetyl chloride hydrochloride (1.645 g., 7.8 mM). The mixture was stirred at 0° C. for four hours and then at room temperature for 15 minutes. The reaction mixture was filtered and the filtrate added dropwise with stirring to diethyl ether (1.5 liters). Stirring was continued for an additional one-half hour and then the granular precipitate filtered off. It was then stirred in methylene chloride (1.5 liters) containing treithylamine (100 mls.) for 45 minutes. The solid was filtered off and this step repeated two more times to give 578 mg. (14.1%) of product.

(3Allylguanidino)Acetyl Chloride Hydrochloride

A solution of allylthiourea (23.2 g., 0.2 m), methyl iodide (3.3 g., 0.3 M) and absolute methanol (100 ml.) was refluxed for two hours and then evaporated in vacuo to an amber glass which crystallized when scratched with a glass rod. The solid was pulverized and triturated with diethyl ether (500 ml.) to give S-methylallylisothiourea as a white, granular solid (50 g.).

A mixture of S-methylallylisothiourea (20.64 g., 0.08 M), glycine (6.0 g., 0.08 M), sodium hydroxide (3.20 g., 0.08 M) and water (80 ml.) was stirred at room temperature for 10 days and then evaporated in vacuo to a glassy residue. The residue was pulverized and washed thoroughly with acetone (10 × 100 ml.). The solid was dried, taken up in water (40 ml.) and refrigerated for four days. The crystals were filtered off, dissolved in water (25 ml.) and 0.1N HCl (71 ml.) added. The solution was freeze-dried and the gummy residue dried over phosphorus pentoxide. It was suspended in dry methylene chloride (100 ml.), phosphorous pentachloride (8.33 g., 0.04 M) added and the suspension stirred at room temperature for 2 hours. The product was filtered off, washed with carbon tetrachloride and dried (1.645 g., 7.8 mM).

EXAMPLE XXVII

A. Acid Addition Salts (Formula I, R=H)

Compounds of formula I wherein R=H are converted to acid addition salts by treating them in aqueous medium with an equivalent amount of the appropriate acid at 0° – 10° C. The mixture is thoroughly stirred for 0.25–1.0 hour and then freeze-dried to afford the salt. In this manner, hydrochloride, hydrobromide, phosphate, citrate, ascorbate, lactate, malate, fumarate, maleate, tartrate, oxalate, glycolate and sulfate are prepared.

B. Acid Addition Salts of Esters (Formula I, R=acyloxy lower alkyl)

The esters of formula I compounds produced by methods described herein are obtained as their hydrochloride salts. Other acid addition salt are produced by passing an aqueous solution of the appropriate ester hydrochloride of formula I through a column of Amberlite IRA-400 (a strongly basic anion exchange resin containing trimethylammonium ion groups, available from Rohm & Haas Co.) operating in the cycle corresponding to the desired salt, e.g., sulfate. A large excess of the resin is used and the product is recovered from the eluate by freeze-drying.

In this manner, the sulfate, citrate, phosphate, oxalate, benzoate hydrobromide, fumarate and tartrate salts are prepared.

Infrared and proton nuclear magnetic resonance spectra of several compounds of this invention having the formula below are listed in Table VI

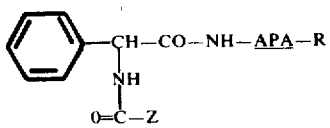

TABLE VI

| Z | R[(1)] | Ir (in KBr; major[(4)] peaks in μ | NMR (ppm; in DMSO[(5)] at 60 Mc |
|---|---|---|---|
| CH$_2$NH—C(NH)NH$_2$ | H | 2.9–3.7 (b), 5.65, 6.0 (b), 6.5 (b), 6.9, 7.2, 7.6, 8.1, 8.4, 8.9 (w), 9.15 (w) | 1.48 (6H,d), 3.68 (1H, s),3.92 (2H,s), 5.38(2H c),5.75(1H,c),7.35(5H,c) 7.85 (2H,c), 8.6 (4H,c) |
| CH$_2$NH—C(NH)NH$_2$ | [(2)]POM[(3)] | 2.9–3.3 (b), 3.45, 5.62 (s), 5.68, 6.0 (b), 6.6, 6.9, 7.2, 7.3, 7.7, 8.5 (b), 9.0, 10.2 | 1.15 (9H,s), 1.48 (6H, d), 4.2 (2H,s), 4.4 (1H,s), 5.45 (2H,c), 5.74 (3H,c), 7.4 (9H,c) 7.95 (2H,c) |
| CH(CH$_3$)NH—C(NH)NH$_2$ | [(3)]POM | 3.1 (b), 3.4 (b), 5.6, 5.7, 5.85, 6.0 (b), 6.5, 6.9, 7.2, 7.3, 7.7, 7.8, 8.35, 8.65, 9.0, 9.75 (w), 10.2 | 1.14 (9H,s), 1.45 (6H, d), 1.5 (3H,d), 4.16 (1H,q), 4.4 (1H,s), 5.45 (2H,c), 5.8 (3H, c), 7.42 (7H,c), 7.98 (2H,c), 8.6 (2H,c) |
| CH$_2$CH$_2$NH—C(NH)NH$_2$ | H | 2.9–3.7 (b), 5.65, 6.0 (b), 6.5, 6.85, 7.2, 7.6, 8.1, 8.4, 8.9 (w), 9.8 (w) | 1.5 (6H,d), 2.54 (2H,c), 3.94 (1H,s), 5.38 (2H, c), 5.75 (1H,c), 7.35 (5H,c), 7.72 (2H,c), 8.7 (4H,c), 3.22 (2H,c) |
| CH$_2$CH$_2$NH—C(NH)NH$_2$ | [(2)]POM[(3)] | 2.9–3.3 (b), 3.4, 5.62 (s), 5.68, 6.0 (b), 6.25, 6.6, 6.9, 7.2, 8.4, 9.0, 10.2 | 1.15 (9H,s), 1.48 (6H, d), 2.65 (2H,c), 3.5 (2H,c), 4.42 (1H,s), 5.42 (2H,c), 5.75 (3H, c), 7.35 (9H,c), 8.2 (2H,c) |
| (CH$_2$)$_3$NH—C(NH)NH$_2$ | POM[(2)] | 2.9–3.4 (b), 3.4, 5.62 (s), 5.68, 6.0 (b), 6.6, 6.9, 7.2, 8.5, 9.1, 10.2 | |
| CH$_2$N(CH$_3$)—C(NH)NH$_2$ | H | 2.9–3.5 (b), 5.65, 6.0, 6.25, 6.7, 6.85, 7.0, 7.2, 7.5, 8.0, 8.9, 9.75 (w) | 1.48 (6H,d), 2.9 (3H,s) 3.65 (1H,s), 3.92 (2H, s), 5.38 (2H,c), 5.76 (1H,c), 7.36 (5H,c), 8.3 (2H,c), 9.0 (3H,c) |
| CH$_2$N(CH$_3$)—C(NH)NH$_2$ | [(2)]POM[(3)] | 2.9–3.3 (b), 3.4, 5.62 (s), 5.68, 6.0 (b), 6.15, 6.6, 7.15, 8.4, 8.7, 9.1, 10.2 | 1.15 (9H,s), 1.46 (6H, d), 2.95 (3H,s), 4.2 (2H,c), 4.4 (1H,s), 5.45 (2H,c), 5.74 (3H, c), 7.0–7.75 (7H,c), 8.2 (3H,c) |
| CH$_2$NH—C(NH)NHCH$_3$ | [(3)]POM | 3.1 (b), 3.4 (b), 5.6, 5.7, 6.0 (b), 6.55, 6.9, 7.15, 7.3, 7.7, 7.8, 8.1, 8.3, 8.65, 9.0, 9.75, 10.25 | 1.14 (9H,s), 1.45 (6H, d), 2.8 (3H,s), 4.1 (2H, s), 4.38 (1H,s), 5.45 (2H,c), 5.75 (3H,c), 7.36 (5H,c), 7.58 (4H,c) |
| CH$_2$NH—(imidazoline) | H | 3.1 (b), 3.4 (b), 5.65, 6.0, 6.25, 6.5, 7.0, 7.2, 7.75, 8.6, 8.85 (w), 9.25 (w) | 1.48 (6H,d), 3.6 (4H, c), 3.7 (1H,s), 3.92 (2H,s), 5.42 (2H,c), 5.75 (1H,s), 7.38 (5H, c), 7.7 (2H,c), 8.8 (2H,c) |
| —C$_6$H$_4$—NH—C(NH)NH$_2$ | H | 2.9–3.7 (b), 5.65, 6.0–6.5 (b), 6.7, 7.25, 7.6, 8.0, 8.9 (w), 9.25 (w), 9.9 (w), | 1.48 (6H,d), 3.98 (1H, s), 5.46 (2H,c), 5.96 (1H,c), 7.38 (7H,c), 8.0 (4H,c), 8.6 (4H,c) |
| —C$_6$H$_4$—NH—C(NH)NH$_2$ | H | 2.9–3.5 (b), 5.65, 6.0 (b), 6.3, 6.6, 6.85, 7.2, 7.6, 8.0, 8.2, 8.65, 8.9, 9.15, 9.4 (w), 9.75 (w) | 1.48 (6H,d), 4.05 (1H, s), 5.48 (2H,c), 5.96 (1H,c), 7.2–8.3 (15H, c) |
| —(S)—NH—C(NH)NH$_2$ | H | 2.9–3.5 (b), 5.65, 6.1 (b), 6.55, 6.9, 7.2, 7.6, 8.0, 8.25, 8.7, 8.9, 9.25 (w), 9.8 (w) | 1.45 (d) and 0.98–2.2(c) (15H), 2.8 (1H,c), 3.96 (1H,s), 5.35 (2H, c), 5.75 (1H,c), 7.38 (5H,c), 7.7 (2H,c), 8.6 (4H,c) |
| CH$_2$—C$_6$H$_4$—NH—C(NH)NH$_2$ | H | 2.9–3.7 (b), 5.65, | 1.48 (6H,d), 3.6 (2H, |

TABLE VI-continued

| Z | R[1] | Ir (in KBr; major[4] peaks in μ) | NMR (ppm; in DMSO[5] at 60 Mc) |
|---|---|---|---|
|  |  | 6.0 (b), 6.6, 6.9, 7.2, 7.6, 8.0, 8.4 (w), 8.6 (w), 8.9 (w), 9.7 (w) | s), 3.94 (1H,s), 5.36 (2H,c), 5.72 (1H,c), 7.28 (9H,c), 8.0 (2H, c), 8.8 (4H,c) |
| CH=CH—⟨⟩—NH—C(NH)NH$_2$ | H | 2.9-3.7 (b), 5.65, 6.1 (b), 6.3 (b), 6.6, 6.85, 7.2, 7.6, 8.0, 8.3, 8.6 (w), 9.0 (w), 9.4 (w), 9.8 (w) | 1.45 (6H,d), 3.98 (1H, s), 5.4 (2H,c), 5.8 (1H, c), 6.55-7.82 (13H,c), 8.8 (4H,c) |
| —⟨⟩—N—C(NH)NH$_2$ | H | 2.9-3.7 (b), 5.6, 6.0, 6.2, 6.6, 6.9, 7.15, 7.6, 8.2, 8.6 (w), 8.9 (w), 9.2 (w), 9.3 (w), 9.75 (w) | 1.45 (d) and 1.2-1.95 (c (10H), 2.3-3.2 (5H, c), 3.94 (1H,s), 5.37 (2H,c), 5.72 (1H,s), 7.38 (5H,c), 8.35 (5H, c) |
| —CHCH$_2$CH$_2$CH$_2$N—C(NH)NH$_2$ | H | 2.9-3.7 (b), 5.65, 6.0 (b), 6.5 (b), 6.9, 7.2, 7.6, 7.75, 7.95, 8.05, 8.65, 8.85, 9.15, 9.5 (w), 10.0 (w) | 1.45 (6H,d), 1.6-2.34 (4H,c), 3.45 (2H,c), 3.92 (1H,s), 4.6 (1H, c), 5.35 (2H,c), 5.75 (1H,s), 7.35 (5H,c), 7.55 (5H,c) |
| CH$_2$NH—C(NH)NHCH$_3$ | H | 2.9-3.5 (b), 5.65, 6.0 (b), 6.5, 6.85, 7.2, 7.55, 8.1, 8.7 (w), 8.9 (w), 9.25 (w) | 1.48 (6H,d), 2.75 (3H, s), 3.92 (3H,s), 5.38 (2H,c), 5.76 (1H,c), 7.35 (5H,c), 7.88 (2H, c), 8.72 (3H,c) |
| CH$_2$—N—CH$_2$CH$_2$—N—C=NH | H | 2.9-3.6 (b), 5.6, 5.9, 6.2, 6.55, 6.85 (w), 7.2, 7.65, 8.0, 8.6 (w), 8.85 (w), 9.1 (w), 9.4 (w), 9.8 (w), 10.6 (w) | 1.45 (6H,d), 3.5 (4H, s), 3.9 (2H,s), 4.1 (1H,s), 5.38 (2H,c), 5.75 (1H,c), 7.35 (5H, c), 7.9 (2H,c), 8.6 (2H,c) |
| ⟨⟩—N—C(NH)NH$_2$ | H | 2.9-3.5 (b), 5.6, 6.0, 6.15, 6.55, 6.85, 7.15, 7.55, 8.2 (w), 8.9 (w), 9.25 (w) | 1.45 (10H,d,c), 2.0-3.9 (5H,c), 3.94 (1H, s), 5.4 (2H,c), 5.75 (1H,c), 7.38 (5H,c), 8.15 (5H,c) |

[1] POM = hydrochloride salt of pivaloyloxymethyl ester.
[2] IR in methylene chloride solution.
[3] NMR in CDCl$_3$; tetramethylsilane used as internal reference.
[4] w = weak; s = shoulder, b = broad
[5] d= doublet; s= singlet; c= complex; q= quartet.
DMSO = dimethyl sulfoxide; tetramethylsilane used as internal reference.

PREPARATION A

General Procedure for α-Aminoacylpenicillin Acyloxyalkyl Esters

The procedure of Daehne et al., J. Med. Chem. 13, 612 (1970) is employed to prepare the title compounds. The procedure comprises acylating the appropriate acyloxyalkyl 6-aminopenicillanate with the appropriate amino acid chloride hydrochloride in a solvent such as methylene chloride in the presence of an acid acceptor (NaHCO$_3$). The ester, amino acid chloride hydrochloride and NaHCO$_3$ are reacted in a molar proportion of about 1.25:1.0:2.5 at 0° – 10° C. for 2 – 3 hours. The mixture is filtered through diatomaceous earth, isopropanol added to the filtrate which is then concentrated in vacuo. Concentration is continued until the product separates. Isopropanol and ether are added to the mixture to complete precipitation of the product.

PREPARATION B

General Procedure for Making Guanidines

1. From S-alkylisothioureas a. A solution of the appropriate amino acid reactant (HOOC—X—NHR$_3$) in concentrated ammonium hydroxide (5–10 moles per mole of amino acid) is treated portionwise with the appropriate S-alkylisothiourea (R$_4$N=C(—SR')NR$_5$R$_6$) (one equivalent) at room temperature. The mixture is allowed to stand overnight and then filtered to provide the product which is washed with water and dried. Ethanol is added if necessary to bring about precipitation of the product.

b. When X is an aryl moiety, the amino acid is used as its sodium salt in water as solvent. The reaction is conducted at 80° C. for 15 – 20 hours and then cooled. The product is recovered according to (a) above.

The guanidino substituted acids listed below are thus prepared from appropriate reactants via method (1):

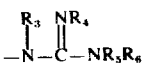

| X | $R_3$ | $R_4$ | $R_5$ | $R_6$ |
|---|---|---|---|---|
| $CH_2$ | H | $CH_3$ | $CH_3$ | H |
| 1,4—$CH_2$—O—$C_6H_4$ | H | H | n—$C_4H_9$ | H |
| 1,4—CH=CH$C_6H_4$ | H | H | H | n—$C_4H_9$ |
| 1,4—$C_6H_4CH_2$ | H | H | $CH_3$ | $C_2H_5$ |
| $CH_3CH$ | H | H | H | $CH_3$ |
| CH=CH—$CH_2$ | H | H | H | H |
| $C_2H_5CH$ | H | H | H | H |
| $(CH_2)_4$ | H | H | H | H |
| 1,1—$C_4H_6$ | H | H | H | H |
| 1,1—$C_3H_4$ | H | H | H | H |
| $CH_2$ | $CH_3$ | H | H | H |
| 1,4—$C_6H_{10}$ | H | H | H | H |
| 1,3—$C_6H_{10}$ | H | H | H | H |
| 1,2—$C_6H_{10}$ | H | H | H | H |

This method is also used for compounds wherein X is alkylene at 25° or 80° C.

| X | $R_3$ | $R_4$ | $R_5$ | $R_6$ |
|---|---|---|---|---|
| 1,4—CH=CH$C_6H_4$ | H | H | H | i—$C_3H_7$ |
| 1,3—$C_6H_{10}$ | H | $C_2H_5$ | H | $C_2H_5$ |
| $CH_2$ | H | $C_7H_7$ | H | $CH_3$ |
| 1,4—$CH_2C_6H_4$ | H | H | i—$C_4H_9$ | H |
| $CH_2$ | H | $C_2H_5$ | H | $CH_3$ |
| $CH_2$ | H | $C_6H_5$ | H | n—$C_4H_9$ |
| $CH_2$ | H | $C_7H_7$ | $C_2H_5$ | H |
| 1,4—$C_6H_4$ | H | $CH_3$ | $CH_3$ | $CH_3$ |
| 1,4—$C_6H_{10}$ | H | $C_6H_5$ | H | $CH_3$ |
| $(CH_2)_4$ | H | $CH_3$ | H | $C_7H_7$ |
| $CH_2$—CH=CH | H | H | n—$C_4H_9$ | H |
| $(CH_2)_3$ | H | H | H | H |
| $(CH_2)_2$ | H | $CH_3$ | $CH_3$ | $C_6H_5$ |
| 1,4—$C_6H_4CH_2$ | H | $CH_3$ | H | H |
| $CH_2$ | H | H | H | $C_6H_5$ |
| 1,4—$C_6H_4$ | H | H | $CH_3$ | H |
| 1,4—$C_6H_{10}$ | $CH_3$ | H | $CH_3$ | H |
| $(CH_2)_4$ | H | H | $CH_3$ | $CH_3$ |
| $CH_2$ | H | H | H | n—$C_4H_9$ |
| $CHCH_3$ | H | H | H | n—$C_3H_7$ |
| $CH_2$ | $CH_3$ | H | H | n—$C_3H_7$ |
| $CH_2$ | $CH_3$ | H | $CH_3$ | $C_2H_5$ |
| $(CH_2)_2$ | $CH_3$ | $CH_3$ | $CH_3$ | H |
| $(CH_2)_4$ | H | H | H | H |
| $(CH_2)_4$ | H | H | $CH_3$ | H |
| $(CH_2)_7$ | H | H | $CH_3$ | H |
| 1,2—$C_6H_{10}$ | H | H | H | $C_6H_5$ |
| 1,2—$C_5H_8$ | H | $CH_3$ | $CH_3$ | $CH_3$ |
| 1,3—$C_6H_{10}$ | H | H | H | n—$C_3H_7$ |
| 1,4—$C_6H_4$ | H | H | H | $C_6H_5$ |
| $(CH_2)_3$ | H | $CH_3$ | H | H |
| $CH_2$ | H | $CH_3$ | H | $C_7H_7$ |
| 1,1—$C_3H_4$ | H | H | H | n—$C_4H_9$ |
| 1,1—$C_7H_{12}$ | H | $CH_3$ | H | H |
| 1,1—$C_6H_{14}$ | H | H | $CH_3$ | $CH_3$ |
| $(CH_2)_2$ | H | H | H | $CH_3$ |
| $CH_2$ | H | $C_6H_5$ | H | $CH_3$ |
| 1,4—$C_6H_4$ | H | $CH_3$ | H | $C_7H_7$ |
| $C_6H_{13}CH$ | H | $CH_3$ | H | H |
| $CH_2$ | H | $CH_3$ | H | H |
| 1,4—$CH_2OC_6H_4$ | $CH_3$ | H | H | H |
| $CH_2$ | H | H | H | $CH_3$ |
| $CHCH_3$ | $CH_3$ | H | H | H |
| $CH_2$ | H | $CH_3$ | $C_2H_5$ | H |
| $CHCH_3$ | H | H | H | H |
| 1,4—$C_6H_4$ | $CH_3$ | H | H | H |
| 1,4—$C_6H_{10}$ | $CH_3$ | H | H | H |
| $(CH_2)_3$ | CH | H | H | H |
| $CH_2$ | n—$C_3H_7$ | H | H | H |
| $CH_2$ | n—$C_4H_9$ | H | H | H |
| $CH_2$ | $C_6H_5$ | H | H | H |
| $CH_2$ | $CH_3$ | H | $CH_3$ | H |
| $CH_2$ | $CH_3$ | H | $C_6H_5$ | H |

2. From Benzoylcyanamid

A mixture of equimolar quantities of the appropriate amino acid and benzoyl cyanamide in ethanol (approximately 50 ml. per mole of amino acid) is evaporated to near dryness on a steam bath. The process is repeated but the mixture is taken to dryness. The residue is refluxed in a slight excess of 1N aqueous sodium hydroxide for one hour, and then cooled, decolorized with activated charcoal, and acidified to about pH 6. The product is filtered, washed with water and dried.

The following guanidino substituted acids are thus prepared from appropriate reactants:

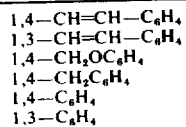

| X |
|---|
| 1,4—CH=CH—$C_6H_4$ |
| 1,3—CH=CH—$C_6H_4$ |
| 1,4—$CH_2OC_6H_4$ |
| 1,4—$CH_2C_6H_4$ |
| 1,4—$C_6H_4$ |
| 1,3—$C_6H_4$ |

PREPARATION C

2-Iminoimidazolidines and
2-Iminohexahydropyrimidines

Reactants having the formula

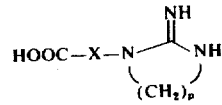

wherein X and $p$ have the values listed below are prepared as described by Rowley et al., J. Am. Chem. Soc. 93, 5542-51 (1971).

The procedure comprises adding cyanogen bromide (5.3 g., 50 mM) dissolved in methanol (7.5 ml.) dropwise over a 3-hour period at room temperature to an aqueous solution of the sodium salt of the appropriate amino acid $HOOC-X-NH(CH_2)_p-NH_2$ (5 mM in 10 ml. of water). The reaction mixture is allowed to stand for 20-30 minutes following completion of addition and the product recovered by filtration. It is washed with cold water and dried.

The following compounds are thus prepared:

| X | p |
|---|---|
| $CH_2CH_2$ | 2 |
| $CHCH_3$ | 3 |
| $CH_2CH_2$ | 3 |
| $(CH_2)_5$ | 2 |
| $(CH_2)_5$ | 3 |
| 1,4—$C_6H_4$ | 2 |
| 1,4—$C_6H_4$ | 3 |
| 1,2—$C_6H_{10}$ | 2 |
| 1,2—$C_6H_{10}$ | 3 |
| 1,3—$C_6H_{10}$ | 2 |
| 1,3—$C_6H_{10}$ | 3 |
| 1,4—$C_6H_{10}$ | 2 |
| 1,4—$C_6H_{10}$ | 3 |
| 1,4—$C_6H_4CH_2$ | 2 |
| 1,4—$C_6H_4CH_2$ | 3 |
| 1,4—CH=CH—$C_6H_4$ | 2 |
| 1,4—CH=CH—$C_6H_4$ | 3 |
| 1,3—CH=CH—$C_6H_4$ | 2 |
| 1,3—CH=CH—$C_6H_4$ | 3 |
| 1,2—CH=CH—$C_6H_4$ | 2 |
| 1,2—CH=CH—$C_6H_4$ | 3 |
| 1,3—$C_6H_4$ | 2 |
| 1,3—$C_6H_4$ | 3 |
| CH=CH—$CH_2$ | 2 |
| 1,4—$CH_2OC_6H_4$ | 2 |
| 1,4—$CH_2OC_6H_4$ | 3 |
| $(CH_2)_7$ | 3 |
| $(CH_2)_3$ | 3 |
| CH=CH—$CH_2$ | 3 |

The amino acid reactants required in this preparation are prepared by reacting the appropriate compound of formula HOOC—X—NH$_2$ with 2-chloroethylamine or 3-chloropropylamine in the presence of potassium iodide (10% by weight based on the chloroalkylamine) as accelerator.

PREPARATION D

1-Guanyl Pyrrolidylcarboxylic Acid Derivatives

Reactants of the formula

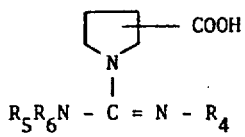

are prepared by treating a solution of 2-(or 3-) pyrrolidine carboxylic acid in an equimolar amount of 4N sodium hydroxide solution at room temperature dropwise over a five-hour period with an equimolar amount of the appropriate S-alkylthiouronium iodide dissolved in the minimum volume of water. The reaction mixture is allowed to stand overnight and then filtered to recover the product. It is purified by dissolution in the minimum amount of ethanol followed by addition of a large excess of acetone containing 10% (v/v) of 95% ethanol. The purified product is filtered off and dried.

The following compounds are thus prepared:

| $R_4$ | $R_5$ | $R_6$ | Isomer |
|---|---|---|---|
| H | H | H | 3 |
| H | CH$_3$ | H | 2 |
| H | CH$_3$ | H | 3 |
| C$_6$H$_5$ | H | C$_2$H$_5$ | 2 |
| CH$_3$ | H | C$_6$H$_5$ | 2 |
| C$_6$H$_5$ | CH$_3$ | H | 2 |
| H | H | C$_6$H$_5$ | 3 |
| C$_7$H$_7$ | C$_2$H$_5$ | H | 3 |
| CH$_3$ | H | CH$_3$ | 2 |
| H | CH$_3$ | CH$_3$ | 2 |
| H | C$_2$H$_5$ | H | 2 |
| CH$_3$ | H | C$_7$H$_7$ | 2 |
| CH$_3$ | CH$_3$ | CH$_3$ | 2 |
| CH$_3$ | H | CH$_3$ | 3 |

PREPARATION E

Reactants of the formula

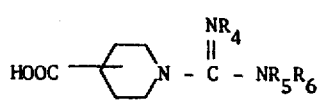

are prepared from the appropriate 2-, 3- or 4-piperidine carboxylic acid by the procedure of Preparation B-(1).

PREPARATION F

2-Imidazolinyl- and 2-(1,4,5,6-Tetrahydropyrimidinyl) Substituted Amino Acids

To a solution of the appropriate amino acid (0.01 M) in aqueous sodium hydroxide (2.50 ml. of 4N) plus sufficient water to provide a clear solution is added 2-methylthioimidazolinium iodide or 2-methylthio-2-(1,4,5,6-tetrahydropyrimidinium) iodide in the minimum amount of water over a five-hour period at room temperature. The reaction mixture is allowed to stand overnight at room temperature. The product is isolated by addition of acetone. It is filtered off and stirred in a large volume of acetone containing 10% (v/v) of 95% ethanol to remove sodium iodide. The acetone-ethanol solution is filtered to give the product.

The following compounds are thus prepared

HOOC—X—NH—\<ring\>(CH$_2$)$_p$

| X* | p |
|---|---|
| CH$_2$ | 3 |
| (CH$_2$)$_5$ | 3 |
| 1,4—C$_6$H$_4$ | 2 |
| 1,4—CH$_2$OC$_6$H$_4$ | 2 |
| (CH$_2$)$_2$ | 3 |
| CH=CH—CH$_2$ | 3 |
| CHCH$_3$ | 3 |
| 1,4—C$_6$H$_4$ | 3 |
| (CH$_2$)$_5$ | 2 |
| (CH$_2$)$_3$ | 2 |
| 1,4—CH$_2$C$_6$H$_4$ | 3 |
| 1,3—CH$_2$C$_6$H$_4$ | 3 |
| 1,4—CH$_2$OC$_6$H$_4$ | 3 |

*When X is an aryl group the reaction is carried out at 80° C. overnight rather than at room temperature.

PREPARATION G

Reactants of the formula

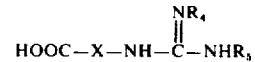

wherein X is as defined above and R$_4$ and R$_5$ when taken together with the guanyl moiety to which they are attached form an imidazolyl or 2-pyrimidinyl group are prepared by the following general procedure:

The appropriate amino acid of formula HOOC — X — NH$_2$ (0.01 M) and 2-chloropyrimidine or 2-chloroimidazole (0.01 M) are reacted in N,N-dimethylformamide (100 ml.) in the presence of triethylamine (0.01 M) as acid acceptor at a temperature of about 80° - 100° C. for 2-3 hours. The reaction mixture is cooled and then filtered and the filtrate evaporated to give the desired product which is used as is.

The compounds listed below are thus prepared. (Im - 2-imidazolyl; PYR = 2-pyrimidinyl)

| X | C(NR$_4$)—NHR$_5$ |
|---|---|
| CH$_2$ | PYR |
| CHC$_2$H$_5$ | Im |
| (CH$_2$)$_2$ | PYR |
| 1,3—C$_6$H$_4$ | PYR |
| 1,4—CH=CH—C$_6$H$_4$ | Im |
| (CH$_2$)$_4$ | PYR |
| 1,4—C$_6$H$_{10}$ | Im |
| 1,3—C$_6$H$_4$ | PYR |
| (CH$_2$)$_3$ | PYR |
| (CH$_2$)$_7$ | Im |
| 1,4—C$_6$H$_4$ | Im |
| CH=CH—CH$_2$ | PYR |
| CH=CH—CH$_2$ | Im |

What is claimed is:

1. A compound of the formula

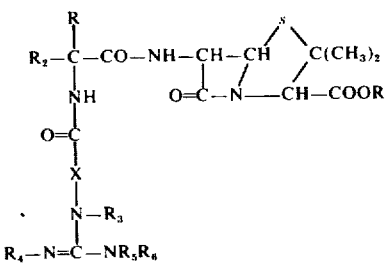

and the pharmaceutically acceptable acid addition salts thereof wherein R is selected from the group consisting of hydrogen and acyloxy lower alkyl wherein acyloxy is selected from the group consisting of lower alkanoyloxy, benzoyloxy and substituted benzoyloxy wherein the substituent is selected from the group consisting of chloro, bromo, fluoro, lower alkyl, lower alkoxy and trifluoromethyl;

$R_1$ is selected from the group consisting of hydrogen, alkyl of from 1 to 14 carbon atoms, cycloalkyl of from 3 to 6 carbon atoms, 1,4-cyclohexadienyl, naphthyl, benzyl, phenethyl, furyl, thienyl, and

wherein Y is selected from the group consisting of hydrogen, nitro, di(lower alkyl)amino, lower alkanoylamino, lower alkyl, lower alkoxy, hydroxy, sulfamyl, chloro, bromo, fluoro, iodo, and trifluoromethyl;

$R_2$ is selected from the group consisting of hydrogen and lower alkyl;

$R_1$ and $R_2$ when taken together with the carbon atom to which they are attached are cycloalkylidene of 3 to 10 carbon atoms;

each of $R_3$ and $R_6$ is selected from the group consisting of hydrogen, lower alkyl, benzyl, and phenyl;

$R_4$ and $R_5$ when taken together with the quanyl moiety to which they are attached form a 5-membered heterocyclic ring selected from the group consisting of 2-imidazolyl, and 2-(2-imidazolinyl) and X is selected from the group consisting of alkylene having from 1 to 7 carbon atoms, phenylene, cycloalkylene having from 3 to 9 carbon atoms, propenylene whose —CH$_2$ group is bound to the adjacent nitrogen; vinylenephenylene, methylene oxyphenylene and phenylenemethylene, each of whose phenylene group is bound to the adjacent nitrogen.

2. A compound according to claim 1 wherein $R_1$ is

each of $R_2$, $R_3$, $R_6$ and R is hydrogen; $R_4$ and $R_5$ together with the guanyl moiety to which they are attached are 2-(2-imidazolinyl) and X is alkylene.

3. A compound according to claim 1 wherein $R_1$ is

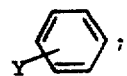

each of $R_2$, $R_3$, $R_6$ and R is hydrogen; $R_4$ and $R_5$ together with the guanyl moiety to which they are attached are 2-imidazolyl and X is alkylene.

4. A compound according to claim 1 wherein $R_1$ is 3-thienyl each of $R_2$, $R_3$, $R_6$ and R is hydrogen and X is methylene.

5. The compound according to claim 2 wherein $R_1$ is phenyl and X is methylene.

6. The compound according to claim 2 wherein $R_1$ is phenyl and X is ethylene.

7. The compound according to claim 3 wherein $R_1$ is 4-hydroxyphenyl and X is methylene.

* * * * *

UNITED STATES PATENT OFFICE
CERTIFICATE OF CORRECTION

PATENT NO. : 3,933,797
DATED : January 20, 1976
INVENTOR(S) : Ernest S. Hamanaka It is certified that error appears in the above-identified patent and that said Letters Patent are hereby corrected as shown below:

Title page, line 3, "(ω-Quanidino" should read -- (ω-Guanidino -- .

Col. 1, line 1, "(ω-Quanidino" should read -- (ω-Guanidino -- ; line 41, "quanidinoaroyl, p-quanidinomethylaroyl" should read -- guanidinoaroyl, p-guanidinomethylaroyl -- ; line 50, "acylando" should read -- acylamido --.

Col. 2, formula I, that portion of the formula reading

N — — — CH-COOR should read N ——— CH-COOR.

Col. 3, formula II, that portion of the formula reading

N — — — CH-COOR should read N ——— CH-COOR;

formula III-A, that portion of the formula reading

N — — — CH-COOR should read N ——— CH-COOR.

Col. 6, in the un-numbered formula in lines 55-60, that portion of the formula reading N — — — CH-C-O should read N ——— CH-C-O .
            ‖                              ‖
            O                              O Col. 8, line 1, "*col.*" should read -- *coli* -- .

Col. 12, line 2, "6-[α-( -" should read -- 6-[α-(ω- -- ; formula V, that portion of the formula reading O=C — — N    should read    O=C ——— N ;

line 37, "Cocket" should read -- Cocker -- ; line 45, "6-[α-( -" should read -- 6-[α-(ω- --

UNITED STATES PATENT OFFICE
CERTIFICATE OF CORRECTION

PATENT NO. : 3,933,797
DATED : January 20, 1976
INVENTOR(S) : Ernest S. Hamanaka It is certified that error appears in the above-identified patent and that said Letters Patent are hereby corrected as shown below:

Col. 14, line 31, "-$CH_2$-O-aminobenzylpenicillin,$C_3H_7$" should read -- -$CH_2$-O-CO-$C_3H_7$-- .

Col. 17, that portion of the formula in Example VII reading

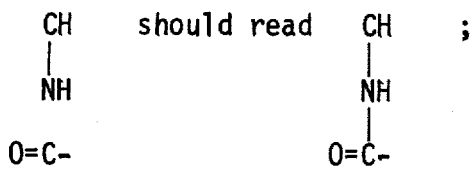

that portion of the formula in Example VIII reading

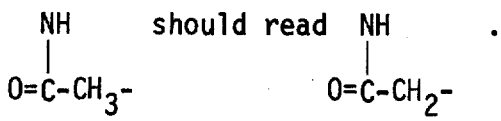

Col. 18, line 52, "methylquanidino)" should read -- methylguanidino -- ; line 64, "2-(β-carboxyethylamino)-2-imidazoline 2-[(carbox-" should read -- 2-(β-carboxyethylamino)-2-imidazoline -- ; line 65, "ymethyl)methylamino]-2-imidazoline" should read -- 2-[(carboxymethyl)methylamino]-2-imidazoline -- .

Col. 19, line 11, "6-[D-2-(3guanidino" should read -- 6-[D-2-phenyl-2-(3-guanidino -- ; line 24, "6-{D-2-[3-(2-" should read -- 6-{D-2-phenyl-2-[3-(2- -- .

Col. 20, line 17, "N-(2-mid chloride" should read -- N-(2-imidazolinyl)glycyl chloride -- .

Col. 22, line 42, "(1 6.)" should read -- (1 g.) -- .

UNITED STATES PATENT OFFICE
CERTIFICATE OF CORRECTION

PATENT NO. : 3,933,797
DATED : January 20, 1976
INVENTOR(S) : Ernest S. Hamanaka It is certified that error appears in the above-identified patent and that said Letters Patent are hereby corrected as shown below:

Col. 24, lines 48-49, delete "-Guandinocin-nomoylamido]" and insert in lieu thereof -- hydrochloride -- .

Col. 26, line 5, "2-(-(guanidino" should read -- 2-(4-guanidino -- ; line 9, "phenoxy)propionic" should read -- phenoxy)butyric -- ; in the un-numbered formula in Example XVII, that portion reading

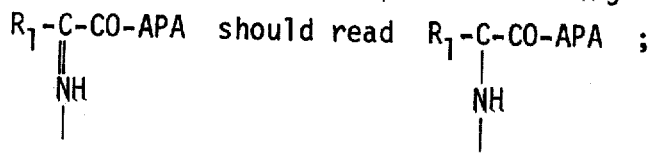

line 6 from the bottom, under the headings "$R_6$","R" and "X" should read, respectively, -- $CH_3$ -- , -- $CH(CH_3)OCOCH_3$ -- and -- $1,4-C_6H_4$ -- .

Col. 28, under the heading "X", the 48th entry reading "$-CH_2-CH=\lambda$" should read -- $-CH_2-CH=$ -- .

Col. 37, line 68, delete "Allylguanidino)Acetyl".

Col. 47, that portion of the first formula in claim 1 reading

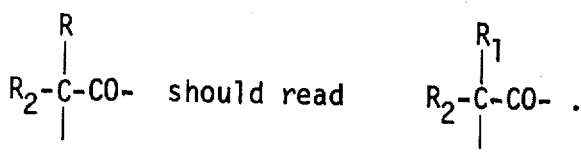

Col. 48, line 3, "quanyl" should read -- guanyl -- .

Signed and Sealed this

Twenty-fourth Day of August 1976

[SEAL]

Attest:

RUTH C. MASON
Attesting Officer

C. MARSHALL DANN
Commissioner of Patents and Trademarks